(12) United States Patent
Nerenberg et al.

(10) Patent No.: US 6,228,870 B1
(45) Date of Patent: May 8, 2001

(54) OXAZOLIDINONES USEFUL AS ALPHA 1A ADRENOCEPTOR ANTAGONISTS

(75) Inventors: Jennie B. Nerenberg, Maple Glen; Mark G. Bock, Hatfield; Michael A. Patane, Harleysville; Harold G. Selnick, Ambler, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/437,841

(22) Filed: Nov. 10, 1999

Related U.S. Application Data

(60) Provisional application No. 60/107,838, filed on Nov. 10, 1998.

(51) Int. Cl.$^7$ ........................ A61K 31/445; C07D 413/12
(52) U.S. Cl. ........................ 514/326; 514/318; 546/194; 546/209
(58) Field of Search ................................... 546/194, 209, 546/318, 326

(56) References Cited

U.S. PATENT DOCUMENTS

| | | |
|---|---|---|
| 3,193,559 | 7/1965 | Regnier et al. . |
| 3,196,152 | 7/1965 | Wright et al. . |
| 3,576,808 | 4/1971 | Schut et al. . |
| 4,089,861 | 5/1978 | Kyburz . |
| 4,145,347 | 3/1979 | L'Italien et al. . |
| 4,377,578 | 3/1983 | Vandenberk et al. . |
| 4,543,318 | 9/1985 | Maeda et al. . |
| 4,661,491 | 4/1987 | Regnier . |
| 4,804,657 | 2/1989 | Kogure et al. . |
| 4,882,431 | 11/1989 | Ishimitsu et al. . |
| 5,698,573 | 12/1997 | Carling et al. . |

FOREIGN PATENT DOCUMENTS

| | | |
|---|---|---|
| 871235 | 1/1960 | (EP) . |
| WO 92/00073 | 1/1992 | (WO) . |
| WO 92/16213 | 10/1992 | (WO) . |
| WO 94/08040 | 4/1994 | (WO) . |
| WO 94/10989 | 5/1994 | (WO) . |
| WO 94/22829 | 10/1994 | (WO) . |
| WO 96/14846 | 5/1996 | (WO) . |
| WO 96/40135 | 12/1996 | (WO) . |
| WO 97/17969 | 5/1997 | (WO) . |
| WO 97/42956 | 11/1997 | (WO) . |
| WO 98/57632 | 12/1998 | (WO) . |
| WO 98/57638 | 12/1998 | (WO) . |
| WO 98/57639 | 12/1998 | (WO) . |
| WO 98/57640 | 12/1998 | (WO) . |
| WO 98/57641 | 12/1998 | (WO) . |
| WO 98/57642 | 12/1998 | (WO) . |
| WO 98/57940 | 12/1998 | (WO) . |
| WO 99/25345 | 12/1998 | (WO) . |
| WO 99/48530 | 9/1999 | (WO) . |

OTHER PUBLICATIONS

Michel et al., Classification of alpha 1–adrenoceptor subtypes, Naunyn–Schmiedeberg's Arch. Pharmacol., (1995) 352:1–10.

*Primary Examiner*—Bernard Dentz
(74) *Attorney, Agent, or Firm*—Catherine D. Fitch; Kenneth R. Walton; Melvin Winokur

(57) ABSTRACT

Novel hydroxymethyl- and alkoxymethyl-oxazolidinone compounds and pharmaceutically acceptable salts thereof are disclosed. The synthesis of these compounds and their use as alpha 1a adrenergic receptor antagonists is also described. One application of these compounds is in the treatment of benign prostatic hyperplasia. These compounds are selective in their ability to relax smooth muscle tissue enriched in the alpha 1a receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia can be achieved.

29 Claims, No Drawings

OXAZOLIDINONES USEFUL AS ALPHA 1A ADRENOCEPTOR ANTAGONISTS

CROSS-REFERENCE TO RELATED APPLICATIONS

This invention claims the benefit of U.S. Provisional Application No. 60/107,838, filed Nov. 10, 1998.

FIELD OF THE INVENTION

This invention relates to certain hydroxymethyl- and alkoxymethyl-oxazolidinone compounds and pharmaceutically acceptable salts thereof, their synthesis, and their use as alpha 1a adrenoceptor antagonists. More particularly, the compounds of the present invention are useful for treating benign prostatic hyperplasia (BPH).

References are made throughout this application to various publications, the disclosures of which are hereby incorporated by reference in their entireties, in order to more fully describe the state of the art to which this invention pertains.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinepluine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., α-*Adrenoreceptors: Molecular Biology, Biochemistry and Pharmacology*, (*Progress in Basic and Clinical Pharmacology* series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Michel et al., *Naunyn-Schmiedeberg's Arch. Pharmacol.* (1995), 352:1–10.

The differences in the alpha adrenergic receptor subtypes have relevance in pathophysio logic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting, the flow of urine through the urethra.

In benign prostatic hyperplasia, the male hormone 5alpha-dihydrotestosterone has been identified as the principal culprit. The continual production of 5α-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.'s product PROSCAR® (finasteride). The effect of this compound is to inhibit the enzyme testosterone 5-α reductase, which converts testosterone into 5α-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfnzosin, which is reported in EP 0 204597 to induce urination in cases of prostatic hyperplasia. Likewise, in WO 92/00073, the selective ability of the R(+) enantiomer of terazosin to bind to adrenergic receptors of the alpha 1 subtype was reported. In addition, in WO 92/16213, combinations of 5α-reductase inhibitory compounds and alphal-adrenergic receptor blockers (terazosin, doxazosin, prazosin, bunazosin, indoramin, alitzosin) were disclosed. However, no information as to the alpha 1d, alpha 1b, or alpha 1a subtype specificity of these compounds was provided as this data and its relevancy to the treatment of BPH was not known. Current therapy for BPH uses existing nonselective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors, in the peripheral vasculature, e.g., hypotension and syncope.

The relatively recent cloning of the human alpha 1a adrenergic receptor (ATCC CRL 11140) and the use of a screening assay utilizing the cloned human alpha 1a receptor has enabled identification of compounds which specifically interact with the human alpha 1a adrerergic receptor. For further description, see WO 94/08040 and WO 94/10989. As disclosed in the instant patent disclosure, a cloned human alpha 1a adrenergic receptor and a method for identifying compounds which bind the human alpha 1a receptor has made possible the identification of selective human alpha 1a adrenergic receptor antagonists useful for treating BPH.

Several classes of compounds have been disclosed to be selective alpha 1a adrenergic receptor antagonists useful for treating BPH. WO 94/22829 discloses, for example, certain 4-(un)substituted phenyl-1,4-dihydropyridine derivatives which are described as potent, se,lective alpha 1a antagonists with weak calcium channel antagonistic activity and which are further described to be anticipated as useful for treating BPH. As another example, WO 96/14846, WO 97/17969 and WO 97/42956 each disclose certain dihydropyrimidine derivatives (e.g., certain 1,2,3,6-tetrahydro-2-oxo-pyrimidine derivatives) which are selective antagonists for the human alpha 1a receptor and useful for treatment of BPH, impotency, cardiac arrhythmia, and other diseases where antagonism of the alpha 1a receptor may be useful. As still another example, WO 96/40135 discloses, inter alia, certain phenylpiperidinyl alkyl saccharin derivatives and their use is selective alpha 1a antagonists.

The instant patent disclosure discloses novel oxazolidinone compounds which selectively bind to the human alpha 1a receptor. These compounds are further tested for binding to other human alpha 1 receptor subtypes, as well as counterscreened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still mother object of the invention is to identify alpha 1a adrenergic receptor antagonists which are useful for relaxing lower urinary tract tissue in animals, preferably mammals, especially humans.

The compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The presence invention provides hydroxymethyl- and alkoxymethyl-oxazolidinone compounds for the treatment of urinary obstruction caused by benign prostatic hyperplasia (BPH). The compounds antagonize the human alpha 1a adrenergic receptor at nanomolar and subnanomolar concentrations while typically exhibiting at least about ten fold lower affinity for the alpha 1d and alpha 1b human adrenergic receptors and many other G-protein coupled receptors. This invention has the advantage over non-selective alpha 1 adrenoceptor antagonists of reduced side effects related to peripheral adrenergic blockade. Such side effects include hypotension, syncope, lethargy, etc.

More particularly, the present invention is a compound of formula (I):

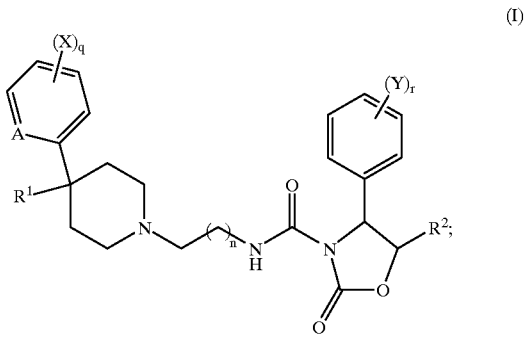

wherein A is CX or N;

X is hydrogen, halo, nitro, cyano, hydroxy, $C_1$–$C_4$ alkyl, $C_1$–$C_4$ alkoxy, fluorinated $C_1$–$C_4$ alkyl, fluorinated $C_1$–$C_4$ alkoxy, $(CH_2)_{1-4}OR^a$, $C_3$–$C_8$ cycloalkyl, fluorinated $C_3$–$C_8$ cycloalkyl, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^A)_2$, or $(CH_2)_{0-4}SO_2R^a$;

Y is hydrogen, halo, nitro, cyano, hydroxy, $C_1$–$C_4$ alkyl, $C_1$–$C_4$ alkoxy, fluorinated $C_1$–$C_4$ alkyl, fluorinated $C_1$–$C_4$ alkoxy, $(CH_2)_{1-4}OR^a$, $C_3$–$C_8$ cycloalkyl, fluorinated $C_3$–$C_8$ cycloalkyl, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^a)_2$, or $(CH_2)_{0-4}SO_2R^a$;

$R^1$ is hydrogen, cyano, $CO_2R^a$, $C(=O)N(R^a)_2$, $C_1$–$C_6$ alkoxy, tetrazole, phenyl, or mono- or poly-substituted phenyl; wherein each of the substituents on the substituted phenyl is independently selected from halo, nitro, cyano, hydroxy, $N(R^a)_2$, $N(R^a)C(=O)R^a$, $N(R^a)C(=O)N(R^a)_2$, $NR^aSO_2R^a$, $NR^aSO_2N(R^a)_2$, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $(CH_2)_{1-4}OR^a$, $(CH_2)_{0-4}CO_2R^a$, $(CH_2)_{0-4}C(=O)N(R^a)_2$, $(CH_2)_{0-4}SO_2N(R^a)_2$, and $(CH_2)_{0-4}SO_2R^a$;

$R^2$ is $CH_2OR^b$;

$R^a$ is hydrogen, $C_1$–$C_6$ alkyl, or fluorinated $C_1$–$C_6$ alkyl;

$R^b$ is hydrogen, $C_1$–$C_6$ allkyl, or $(CH_2)_{1-4}CF_3$;

n is an integer of from 1 to 3; and q and r are each independently integers of from 0 to 3;

or a pharmaceutically acceptable salt thereof.

The presernt invention also includes pharmaceutical compositions, methods of preparing pharmaceutical compositions, and methods of treatment.

These and other embodiments, aspects and features of the present invention are either further described in or will be apparent from the ensuing description, examples and appended claims.

DETAILED DESCRIPTION OF THE INVENTION

The present invention includes oxazolidinone compounds of Formula (I) above. These compounds and their pharmaceutically acceptable salts are useful as selective alpha 1a antagonists.

In a first embodiment, the present invention is a compound is of formula (II)

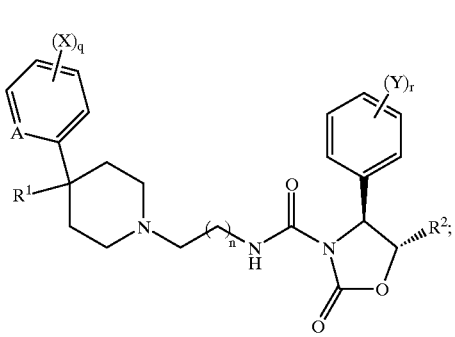

(II)

and all variables are as originally defined above;
or a pharmaceutically acceptable salt thereof.

In a second embodiment, the present invention is a compound of Formula (I), wherein
X is hydrogen, halo, nitro, cyano, hydroxy, $C_1$–$C_4$ alkyl, $C_1$–$C_4$ alkoxy, $(CH_2)_{1-3}OR^a$, $(CH_2)_{0-3}CF_3$, $OCF_3$, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^a)_2$, or $(CH_2)_{0-4}SO_2R^a$;
Y is hydrogen, halo, nitro, cyano, hydroxy, $C_1$–$C_4$ alkyl, $C_1$–$C_4$ alkoxy, $(CH_2)_{1-3}OR^a$, $(CH_2)_{0-3}CF_3$, $OCF_3$, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^a)_2$, or $(CH_2)_{0-4}SO_2R^a$;
$R^1$ is hydrogen, cyano, $CO_2R^a$, $C(=O)N(R^a)_2$, $C_1$–$C_4$ alkoxy, or tetrazole;
$R^a$ is hydrogen, $C_1$–$C_4$ alkyl, or $(CH_2)_{0-3}CF_3$;
q and r are each independently integers of from 0 to 2;
and all other variables are as originally defined above;
or a pharmaceutically acceptable salt thereof.

In a third embodiment, the present invention is a compound of Formula (I), wherein
A is CX;
X is hydrogen, halo, nitro, cyano, hydroxy, $C_1$–$C_4$ alkyl, $C_1$–$C_4$ alkoxy, $(CH_2)_{1-3}OR^a$, $(CH_2)_{0-3}CF_3$, $OCF_3$, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^a)_2$, or $(CH_2)_{0-4}SO_2R^a$;
Y is hydrogen, halo, nitro, cyano, hydroxy, $C_1$–$C_4$ alkyl, $C_1$–$C_4$ alkoxy, $(CH_2)_{1-3}OR^a$, $(CH_2)_{0-3}CF_3$, $OCF_3$, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^a)_2$, or $(CH_2)_{0-4}SO_2R^a$;
$R^1$ is hydrogen, cyano, $CO_2R^a$, $C(=O)N(R^a)_2$, $C_1$–$C_4$ alkoxy, or tetrazole;
$R^a$ is hydrogen, $C_1$–$C_4$ alkyl, or $(CH_2)_{0-3}CF_3$;
$R^b$ is hydrogen, $C_1$–$C_4$ alkyl, or $(CH_2)_{1-3}CF_3$;
q and r are each independently integers of from 0 to 2;
and all other variables are as originally defined above;
or a pharmaceutically acceptable salt thereof.

In a first class, the present invention is a compound of Formula (I), wherein
X is hydrogen, halo, nitro, cyano, hydroxy, methyl, ethyl, methoxy, ethoxy, or $CF_3$;
Y is hydrogen, halo, nitrco, cyano, hydroxy, methyl, ethyl, methoxy, ethoxy or $CF_3$;
$R^1$ is hydrogen, cyano, $CO_2CH_3$, $CO_2CH_2CH_3$, methoxy, or ethoxy;
$R^2$ is $CH_2OH$ or $CH_2OCH_3$;
and all other variables are as defined for the third embodiment;
or a pharmaceutically acceptable salt thereof.

In a first sub-class, the present invention is a compound of Formula (I), wherein
X is hydrogen, fluoro or cyano;
Y is hydrogen or fluoro;
and all other variables are as defined for the first class;
or a pharmaceutically acceptable salt thereof.

In a second sub-class, the present invention is a compound of formula (III)

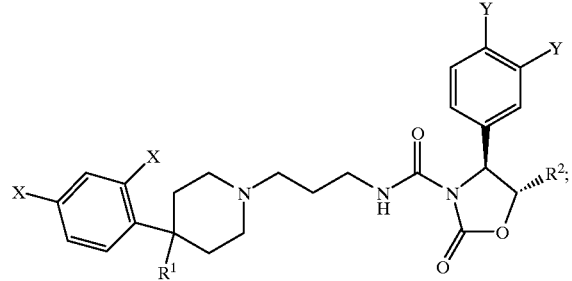

(III)

wherein all of the variables are as defined above for the first class;
or a pharmaceutically acceptable salt thereof.

In one aspect, the present invention is a compound of formula (III), wherein
X is hydrogen, fluoro or cyano;
Y is hydrogen or fluoro;
and all other variables are as defined for the second sub-class;
or a pharmaceutically acceptable salt thereof.

Exemplifying the invention is a compound selected from the group consisting of:
(4S,5R)-4-(3,4-difluorophenyl)-5-hydroxymethyl-2-oxo-oxazolidine-3-carboxylic acid {3-[4-(2-cyano-4-fluorophenyl)piperidin-1-yl]propyl}amide; (4S,5R)-4-(3,4-difluorophenyl)-5-hydroxymethyl-2-oxo-oxazolidine-3-carboxylic acid {3-[4-(4-fluorophenyl)piperidin-1-yl]propyl}amide;
(4S,5R)-4-(3,4-difluorophenyl)-5-hydroxymethyl-2-oxo-oxazolidine-3-carboxylic acid {3-[4-(2-cyanophenml)piperidin-1-yl]propyl}amide;
(4S,5R)-4-(3,4-difluorophenyl)-5-hydroxymethyl-2-oxo-oxazolidine-3-carboxylic acid {3-[4-cyano-4-(2,4-(difluorophenyl)piperidin-1-yl]propyl}amide;
(4S,5R)-4-(3,4-difluororhenyl)-5-hydroxyrnethyl-2-oxo-oxazolidine-3-carboxylic acid {3-[4-cyano-4-(2-cyanophenyl)piperidin-1-yl]propyl}amide;

(4S,5R)-4-(3,4-difluorophenyl)-5-methoxymethyl-2-oxo-oxazolidine-3-carboxylic acid {3-[4-(2-cyanophenyl)piperidin-1-yl]propyl}amide;

(4S,5R)-4-(3,4-difluorophenyl)-5-methoxymethyl-2-oxo-oxazolidine-3-carboxylic acid {3-[4-cyano-4-(2,4-difluorophenyl)piperidin-1-yl]propyl}amide;

(4S,5R)-4-(3,4-difluorophenyl)-5-methoxymethyl-2-oxo-oxazolidine-3-carboxylic acid {3-[4-(2-cyano-4-fluorophenyl)piperidin-1-yl]propyl}amide;

and pharmaceutically acceptable salts thereof.

Further exemplifying the invention is (4S,5R)-4-(3,4-difluorophenyl)-5-hydroxymethyl-2-oxo-oxazolidine-3-carboxylic acid {3-[4-(2-cyano-4-fluorophenyl)piperidin-1-yl]propyl}amide, having the structure

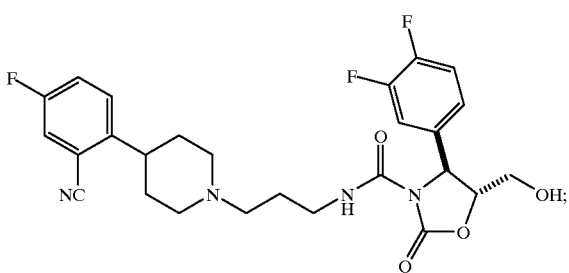

or a pharmaceutically acceptable salt thereof.

Also exemplifying the invention is (4S,5R)-4-(3,4-difluorophenyl)-5-hydroxymethyl-2-oxo-oxazolidine-3-carboxylic acid {3-[4-cyano-4-(2,4-difluorophenyl)piperidir-1-yl]propyl}amide, having the structure

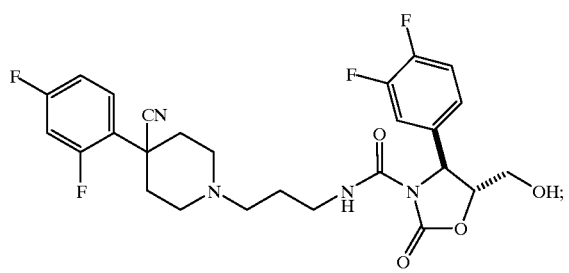

or a pharmaceutically acceptable salt thereof.

The present invention also includes a pharmaceutical composition comprising a therapeutically effective amount of any of the compounds described above and a pharmaceutically acceptable carrier. In one embodiment is a pharmaceutical composition made by combining any of the compounds described above and a pharmaceutically acceptable carrier. The present invention further includes a process for making a pharmaceutical composition comprising combining any of the compounds described above and a pharmaceutically acceptable carrier.

The present invention further includes a pharmaceutical composition as described in the preceding paragraph further comprising a therapeutically effective amount of a testosterone 5-alpha reductase inhibitor. In one embodiment, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor), or a dual type 1 and type 2 testosterone 5-alpha reductase inhibitor. In another embodiment, the testosterone 5-alpha reductase inhibitor is a type 2 testosterone 5-alpha reductase inhibitor. The testosterone 5-alpha reductase inhibitor is suitably finasteride.

The present invention also includes a method of treating benign prostatic hyperplasia in a subject in need thereof which comprises administering to the subject a therapeutically effective amount of any of the compounds (or any of the compositions) described above. In one embodiment of the method of treating BPH, the compound (or composition) does not cause a fall in blood pressure at dosages effective to alleviate BPH. In another embodiment of the method of treating BPH, the compound is administered in combination with a testosterone 5-alpha reductase inhibitor. A suitable testosterone 5-alpha reductase inhibitor for use in the method is finasteride.

The present invention also includes a method of inhibiting contraction of prostate tissue or relaxincg lower urinary tract tissue in a subject in need thereof which comprises administering to the subject a therapeutically effective amount of any of the compounds (or any of the compositions) described above. In one embodiment of the method of inhibiting contraction of prostate tissue or relaxing lower urinary tract tissue, the compound (or composition) additionally does not cause a fall in blood pressure at dosages effective to inhibit contraction of prostate tissue. In another embodiment, the compound is administered in combination with a testosterone 5-alpha reductase inhibitor; the testosterone 5-alpha reductase inhibitor is suitably finasteride.

The present invention also includes a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see K. A. Vatz, *Headache* (1997), 37:107–108) and cardiac arrhythmia.

The present invention also includes the use of any of the compounds described above in the preparation of a medicament for: a) treating benign prostatic hyperplasia; b) relaxing lower urinary tract tissue; or c) inhibiting contraction of prostate tissue; in a subject in need thereof.

The present invention further includes the use of any of the alpha 1a antagonist compounds described above and a 5-alpha reductase inhibitor for the manufacture of a medicanent for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

As used herein, the term "$C_1$–$C_6$ alkyl" means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl.

The term "$C_1$–$C_6$ alkoxy" means an —O-alkyl group wherein alkyl is $C_1$ to $C_6$ alkyl. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy.

The term "$C_3$–$C_8$ cycloalkyl" means a cyclic ring of an alkane having three to eight total carbon atoms (i.e., cyclopropyl, cyclobutyl, cyclopentyl, cyclohexyl, cycloheptyl or cyclooctyl). "$C_3$–$C_6$ cycloalkyl" refers to a cyclic ring selected from cyclopropyl, cyclobutyl, cyclopentyl, and cyclohexyl.

The term "halo" (which may alternatively be referred to as "halogen") refers to fluoro, chloro, bromo, and iodo (alternatively fluorine, chlorine, bromine and iodine).

The term "fluorinated $C_1$–$C_6$ alkyl" (which may alternatively be referred to as "$C_1$–$C_6$ fluoroalkyl") means a $C_1$ to $C_6$ linear or branched alkyl group as defined above with one or more fluorine substituents. The term "fluorinated $C_1$–$C_4$ alkyl" has an analogous meaning. Representative examples of suitable fluoroalkyls include the series $(CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "fluorinated $C_3$–$C_8$ cycloalkyl" (which may alternatively be referred to as "$C_3$–$C_8$ fluorocycloalkyl") means a cycloalkyl group as defined above with one or more fluorine substituents. "Fluorinated $C_3$–$C_6$ cycloalkyl" has an analogous meaning. Representative examples of suitable fluorocycloalkyls include all isomers of fluorocyclohexyl (i.e., 1-, 2-, 3-, and 4-fluorocyclohexyl), difluorocyclohexyl (e.g., 2,4-difluorocyclohexyl, 3,4-difluorocyclohexyl, etc.), fluorocyclopentyl, and so forth.

The term "fluorinated $C_1$–$C_6$ alkoxy" (which may alternatively be referred to as "$C_1$–$C_6$ fluoroalkoxy") means a $C_1$–$C_6$ alkoxy group as defined above wherein the alkyl moiety has one or more fluorine substituents. "Fluorinated $C_1$–$C_4$ alkoxy" has an analogous meaning. Representative examples include the series $O(CH_2)_{0-4}CF_3$ (i.e., trifluoromethoxy, 2,2,2-trifluoroethoxy, 3,3,3-trifluoro-n-propoxy, etc.), 1,1,1,3,3,3-hexafluoroisopropoxy, and so forth.

The term "heterocyclic" (which may alternatively be referred to as "heterocycle") refers to pyridyl, pyridyl N-oxide, pyrazinyl, thienyl, thiazolyl, furanyl and quinazolyl. The heterocyclic ring may be attached at any heteroatom or carbon atom which results in the creation of a stable structure.

The term "thienyl," as used herein, refers to the group

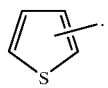

The term "aryl" refers to phenyl, substituted phenyl, naphthyl, and substituted naphthyl.

The term "heteroaryl" refers to heterocyclic or substituted heterocyclic.

The term "substituted" includes mono- and poly-substitution by a named substituent to the (extent such single and multiple substitution is chemically allowed.

The term "poly-substituted" refers herein to multiple degrees of substitution by a named substituent or substituents. For example, the term "poly-substituted phenyl" denotes di-, tri-, tetra- and penta-substitution by a named substituent or a combination of named substituents (e.g., "di-substituted phenyl wherein each substituent is independently selected from fluoro, methoxy and cyano" represents such moieties as 2,4-difluorophenyl, 3,4-difluorophenyl, 2-methoxy-4-fluorophenyl, 2-fluoro-4-cyanophenyl, 2-cyano-4-fluorophenyl, 3-cyano-4-fluorophenyl, etc.)

It is understood that the definition of a substituent (e.g., X) at a particular location in a molecule is independent of its definition at other locations in the molecule. Thus, for example, when q=2 and X at one location is halo, X at the other location can be hydrogen, halo, nitro, etc. It is also understood that the definition of a variable (e.g., $R^a$) at a particular location in a molecule is independent of its definitions at other locations in that molecule. Thus, for example, when q=2 and X at one location is $(CH_2)_{0-4}CO_2R^a$=$CO_2H$, the X at the other location on the ring can be any one of $CO_2H$, $CO_2Me$, $CO_2Et$, $CO_2Pr$, $CH_2CO_2H$, $CH_2CO_2Me$, $CH_2CO_2Et$, $CH_2CO_2Pr$, $(CH_2)_2CO_2H$, etc.

It is also understood that the definition of a substituent or variable at a particular location in a molecule is independent of the definition of another occurrence of the same substituent or variable at the same location. Thus, $N(R^a)_2$ represents groups such as —$NH_2$, —NHMe, —NHEt, —$NMe_2$, —N(Me)Et, etc.

Other embodiments for the variables and substituents set forth in Formula (I) include the following:

A is CX.

X is hydrogen, halo, nitro, cyano, hydroxy, $C_1$–$C_4$ alkyl, $C_1$–$C_4$ alkoxy, $(CH_2)_{1-3}OR^a$, $((CH_2)_{0-3}CF_3$, $OCF_3$, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^a)_2$, or $(CH_2)_{0-4}SO_2R^a$; or is hydrogen, halo, nitro, cyano, hydroxy, methyl, ethyl, methoxy, ethoxy, or $CF_3$; or is hydrogen, fluoro or cyano.

Y is hydrogen, halo, nitro, cyano, hydroxy, $C_1$–$C_4$ alkyl, $C_1$–$C_4$ alkoxy, $(CH_2)_{1-3}OR^a$, $(CH_2)_{0-3}CF_3$, $OCF_3$, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^a)_2$, or $(CH_2)_{0-4}SO_2R^a$; or is hydrogen, halo, nitro, cyano, hydroxy, methyl, ethyl, methoxy, ethoxy or $CF_3$; or is hydrogen or fluoro; or is fluoro.

$R^1$ is hydrogen, cyano, $CO_2R^a$, C(=O)N($R^a$)$_2$, $C_1$–$C_4$ alkoxy, or tetrazole; or is hydrogen, cyano, $CO_2CH_3$, $CO_2CH_2CH_3$, methoxy, or ethoxy; or is hydrogen or cyano.

$R^2$ is $CH_2OH$ or $CH_2OCH_3$.

$R^a$ is hydrogen, $C_1$–$C_4$ alkyl, or $(CH_2)_{0-3}CF_3$; or is hydrogen, methyl, ethyl, or $CF_3$.

$R^b$ is hydrogen, $C_1$–$C_4$ alkyl, or $(CH_2)_{0-3}CF_3$; or is hydrogen, methyl, ethyl, $CF_3$, or $(CH_2)_{0-3}CF_3$; or is hydrogen, methyl, or ethyl.

n is 2 or 3; or is 2.

q and r are each independently 0 to 2; or are independently 1 or 2.

Representative compounds of the present invention exhibit high selectivity for the human alpha 1a adrenergic receptor. One implication of this selectivity is that these compounds display selectivity for lowering intraurethral pressure without substantially affecting diastolic blood pressure.

Representative compounds of this invention display submicromolar affinity for the human alpha 1a adrenergic receptor subtype while typically displaying at least about ten-fold lower affinity for the human alpha 1d and alpha 1b adrenergic receptor subtypes, and many other G-protein coupled human receptors. Particular representative compounds of this invention exhibit nanomolar and subnanomolar affinity for the human alpha 1a adrenergic receptor subtype while displaying at least about 100 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors). Still other compounds of this invention exhibit nanomolar and subnanomolar affinity for the human alpha 1a adrenergic receptor subtype while displaying at least about 500 fold lower affinity for the human alpha 1d and alpha 1b adrenergic receptor subtypes. Compounds of the invention can have favorable selectivity for the human alpha 1a receptor subtype over the alpha 1b and 1d subtypes and over other G-protein coupled receptors in combination with a beneficial pharmacokinetic profile.

These compounds are administered in dosages effective to antagonize the alpha 1a receptor where such treatment is needed; e.g., treatment of BPH. For use in medicine, the salts of the compounds of this invention refer to non-toxic "pharmaceutically acceptable salts." Other salts may, however, be useful in the preparation of the compounds according to the invention or in the prepartion of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, benzenesulfonate, benzoate, bicarbonate, bisulfate, bitartrate, borate, bromide, calcium, camsylate, carbonate, chloride, clavulanate, citrate, dihydrochloride, edetate, e disylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Compounds of this invention are used to reduce the acute symptoms of BPH. Thus, compounds of this invention may be used alone or in combination with more long-term anti-BPH therapeutics, such as testosterone 5-a reductase inhibitors, including PROSCAR® (Finasteride). Aside from their utility as anti-BPH agents, these compounds may be used to induce highly tissue-specific, localized alpha 1a adrenergic receptor blockide whenever this is desired. Effects of this blockade include reduction of intra-ocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient Conventional procedures for the selection and preparation of suitable prodrug derivatives are described, for example, in Design of Prodrugs, ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the coirpounds of the present invention may form solvates with water (i.e., hydrates) or common organic solvents. Such solvates are also encompassed within the scope of this invention.

The term "selective alpha 1a adrenergic receptor antagonist," as used herein, refers to an alpha 1a antagonist compound which is at least about ten fold selective for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms; of the disease being treated.

The present invention includes pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" encompasses a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqiueous suspensions include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixtures of stereoisomers, these isomers may be separated by conventional techniques such as preparative chromatography. The compounds may be prepared in racernic form, or individual enantiomers may be prepared either by enantiospecific synthesis or by resolution. The compounds may, for example, be resolved into their component enantiomers by standard techniques, such as the formation of diastereomgric pairs by salt formation with an optically active acid, such as (–)-di-p-toluoyl-d-tartiric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

The specificity of binding of compounds showing affinity for the alpha 1a receptor is shown by comparing affinity to membranes obtained from transfected cell lines that express the aLlpha 1a receptor and membranes from cell lines or tissues known to express other types of alpha (e.g., alpha 1d, alpha 1b) or beta adrenergic receptors. Expression of the cloned human alpha 1d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergi receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism mayt further be defined by counter screening. This is accomplished according to methods known in the art using other receptors responsible for mediating diverse biological functions. [See e.g., PCT International Application Publication No. WO94/10989, published May 26, 1994; U.S. Pat. No. 5,403,847, issued Apr. 4, 1995]. Compounds which are both selective amongst the various human alpha1 adrenergic receptor subtypes and which have low affinity for other receptors, such as the alpha 2 adrenergic receptors, the β-adrenergic receptors, the muscarinic receptors, the serotonin receptors, histamine receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-othylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range; e.g., from about 0.01 to about 1000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to about 10 mg/kg of body weight per day, and especially from about 0.001 mg/kg to about 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this invention is administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5a-reductase inhibitors have been described in WO93/23420, EP 0572166; WO 93/23050; WO93/23038,; WO93/23048; WO93/23041; WO93/23040; WO93/23039; WO93/23376; WO93/23419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one embodiment of the present invention, a method of treating BPH is provided which comprises administering to a subject in need of treatment any of the compounds of the present invention in combination with finasteride effective to treat BPH. The dosage of finasteride administered to the subject is from about 0.01 mg per subject per day to about 50 mg per subject per day in combination with an alpha 1a antagonist. In one aspect, the dosage of finasteride in the combination is from about 0.2 mg per subject per day to about 10 mg per subject per day, and, in another aspect, from about 1 to about 7 mg per subject to day (e.g., about 5 mg per subject per day).

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7β-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. No. 4,377,584 and U.S. Pat. No. 4,760,071 which describe, dosages and formulations for 5a-reductase inhibitors.

Abbreviations used in the instant specification, particularly the Schemes and Examples, are as follows:

Bn=benzyl

Boc or BOC=t-butyloxycarbonyl $(DHQ)_2PHAL$=bis(dihydroquinidyl)phthalazine

CSA=10-camphorsulfonic acid

DMF=N,N-dimethylformamide

DMSO=dimethylsulfoxide

EDC=1-(3-dimethylaminopropyl)-3-ethyl carbodiimide hydrochloride

EDTA=ethylenediamine tetraacetic acid

Et=ethyl

FAB MS=fast atom bombardment mass spectroscopy

HOBt=1-hydroxy benzotriazole hydrate i-$Pr_2$NEt=diisopropylethylamine

LDA=lithium diusopropyl amide

LiHMDS=lithium bis(trimethylsilyl)amide

Me=methyl

MeOH=methanol

M.P.=melting point

NMR=nuclear magnetic resonance $PhNTf_2$=N-plienyltrifluoromethanesulfonimide

Pr=propyl t-BuOCl=t-butylhypochlorite

Tf=triflic or triflate $Tf_2O$=triflic anhydride

THF=tetrahydrofuran

TsOH=p-toluenesulfonic acid

The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Many of the compounds claimed within this invention can be assembled via Schemes I and II shown below.

Scheme I describes the preparation of primary amines (4 and 6) suitable for the preparation of many of the compounds of the present invention. In Scheme I, part A, 1-Boc-4-piperidone or a substituted analog (1) can be treated with LDA followed by N-phenyltrifluoromethanesulfonimide to provide the corresponding triflate 2. Palladium catalyzed coupling with an aryl or heteroaryl organozincate RZnX, followed by hydrogenation of the resulting alkene and nitrogen deprotection with HCl(g) affords a substituted piperidine hydrochloride of type 3. Alkylation with 3-bromo-1-Boc-propylariine in the presence of triethylamine followed by deprotection with HCl(g) affords amine 4.

As shown in Scheme I, part B, aryl- and heteroaryl-acetonitriles can be treated with a base such as NaH or cesium carbonate and with bis-(2-chloroethyl)-tert-butoxycarbonylamine to afford the piperidine derivatives of type 5. Deprotection and alkylation as described before gives access to amines of type 6.

Oxazolidinones substituted with hydroxyalkyl and alkoxyalkyl can be prepared by hydroxyaminaation of olefins to provide protected aminoalcohols, using procedures as described in Sharpless et al., Angew. *Chem. Int. Ed. Engl.* (1996), 35: 2813. Deprotection under standard conditions followed by a phosgene equivalent to mediate cyclization provides the substituted oxazolidinone ring system. Deprotonation with a strong base, for example, lithium bis(trimethylsilyl)amide, and addition to a THF solution of p-nitrophenylchloroformate produces a stable, isolable "activated" oxazolidinorie.

The oxazolidinones were prepared in enantiomer-enriched form and the assignments of (4S,5S) were made in accordance with Sharpless et al., Angew. *Chem. Int. Ed. Engl.* (1996), 35: 2813.

Selective acylation of the primary amines was accomplished by treatment of the amines with nearly equimolar quantities of the activated oxazolidinones.

Scheme II provides further illustration of the preparation of the compounds of the present invention. Scheme II, Part A describes the preparation of hydroxymethyl oxazolidirione compounds of the invention. A cinnamic acid is esterified with methanol in the presence of acid to form the corresponding methyl cinnamate, which is reacted with benzylcarbamate in the presence of t-butyl hypochlorite, base, an osrmium catalyst, and a phthalazine ligand to form an asymmetric hydroxycarbamate. The hydroxycarbamate is deprotected to the corresponding aminoalcoiol, which is cyclized to the oxazolidinone 7, whose methylcarboxylate group is reduced via $LiBH_4$ to the hydroxymethyl-substituted oxazolidinone 8. The hydroxy group on 8 is protected by conversion of 8 to the dihydropyranyloxymethyl derivative 9, which is deprotonated with lithium bis(trimethylsilyl)amide, and converted to the activated p-nitrophenyl analog 10 by reaction with p-nitrophenylchloroformate. Compound 10 is then coupled with an appropriate primary amine (e.g., 4 or 6) to form 11, which is then deprotected to give the hydroxymethyl oxazolidinone 12.

Scheme II, Part B describes the preparation of alkoxymethyl oxazolidinone compounds of the invention. Hydroxymethyloxazolidinone component 8 is alkylated with R'I (R'=$C_1$–$C_6$ alkyl, or fluorinated $C_1$–$C_6$ alkyl) to form the alkoxymethyl derivative 13, which is converted to the activated p-nitrophenyl analog 14 by reaction with p-nitrophenylchloroformate. Compound 14 is then coupled with an appropriate primary amine (e.g., 4 or 6) to form compound 15.

SCHEME I
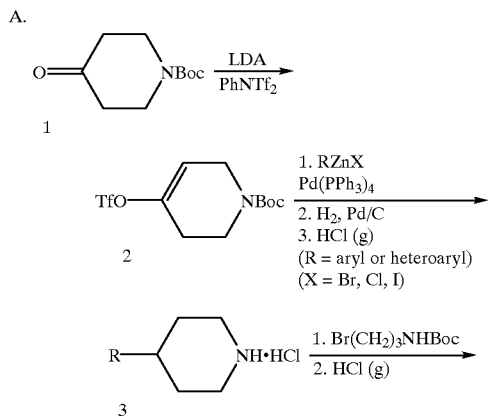
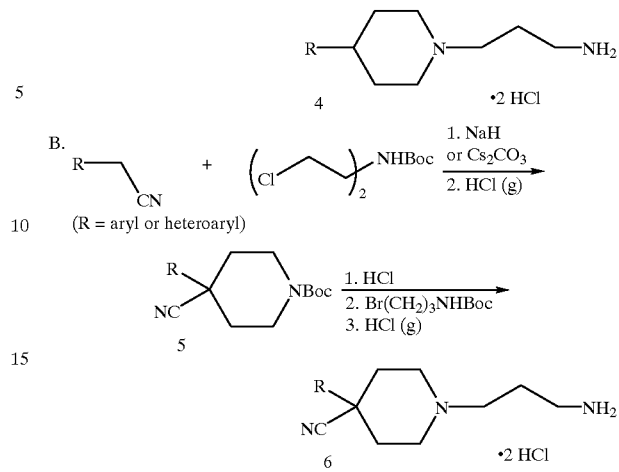
SCHEME II
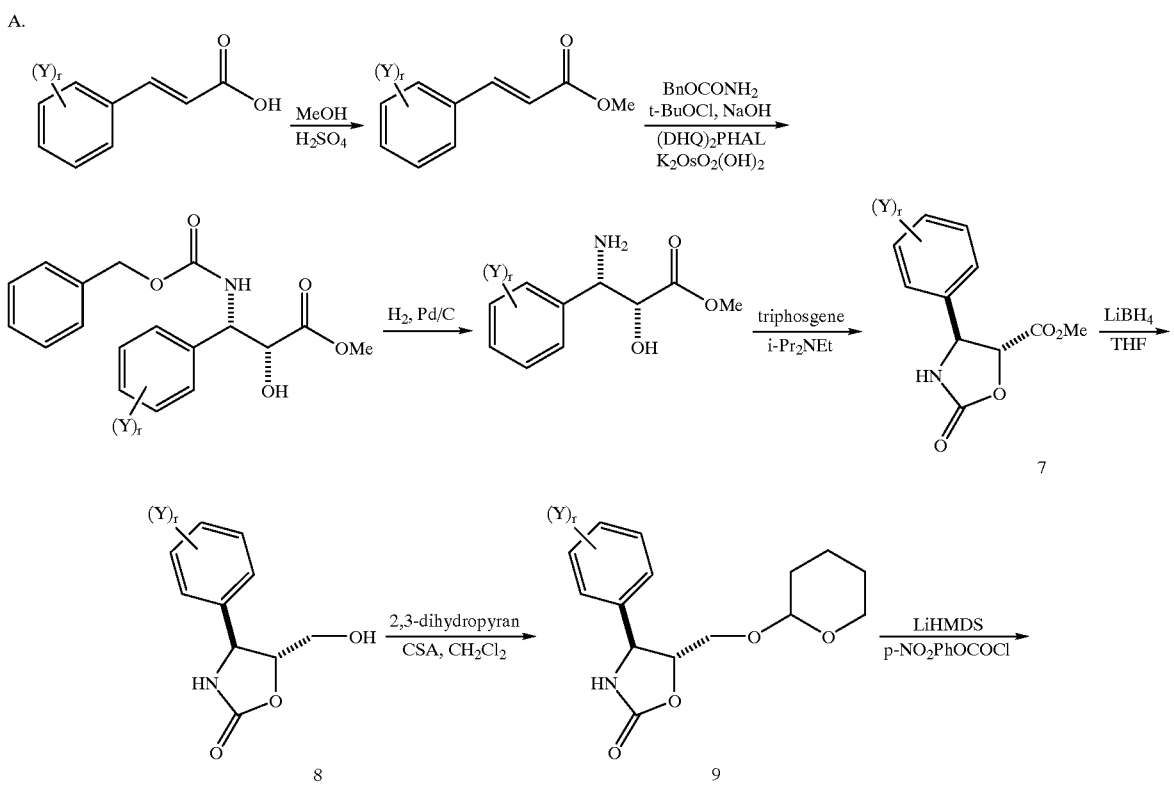

-continued
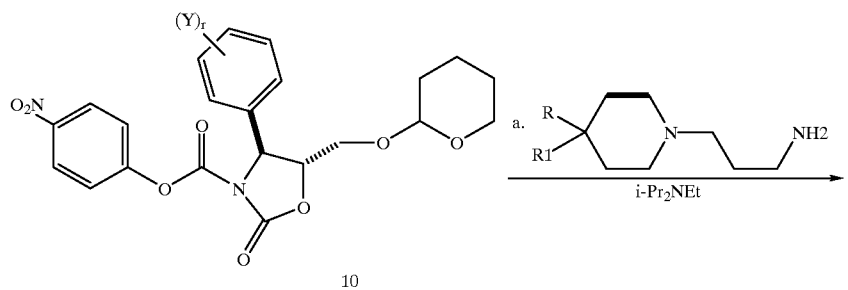
10
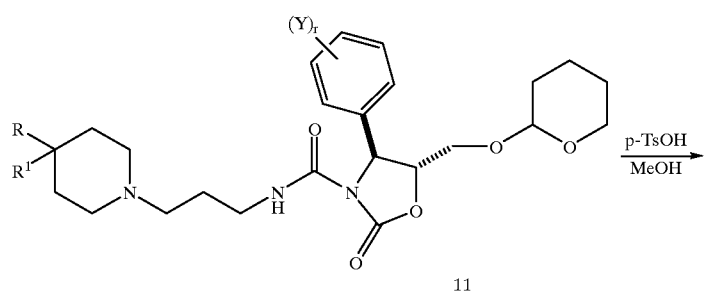
11
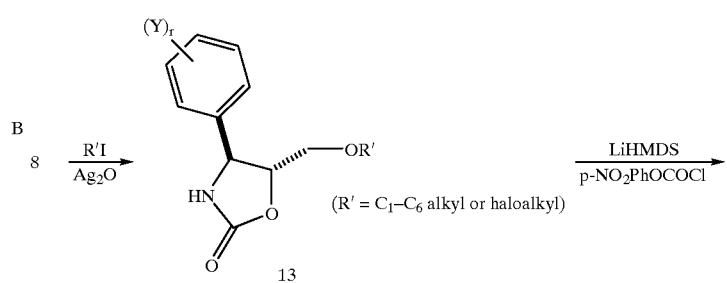
12
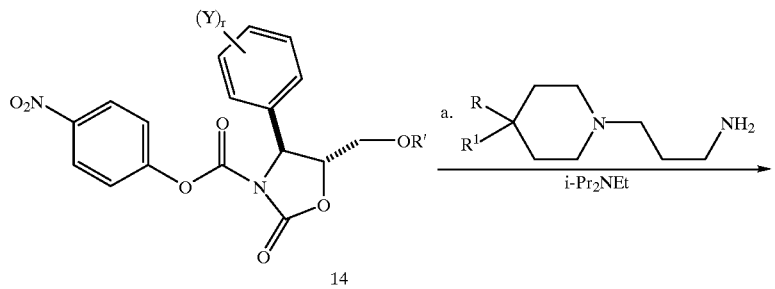

-continued

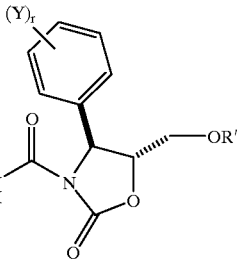

15

The following Examples further describe and illustrate the invention and its practice and are not to be construed a limiting the scope or spirit of the invention.

EXAMPLE 1

2-[1-(3-Aminopropyl)-piperidin-4-yl]-5-fluorobenzonitrile hydrochloride

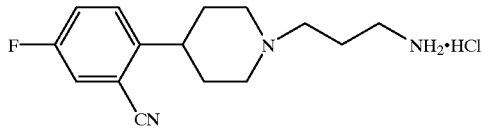

Step A. Trifluoromethanesulfonic acid[1-tert-butoxycarbonyl-(1,2,3,6-tetrahydro-pyridin-4-yl)]Ester

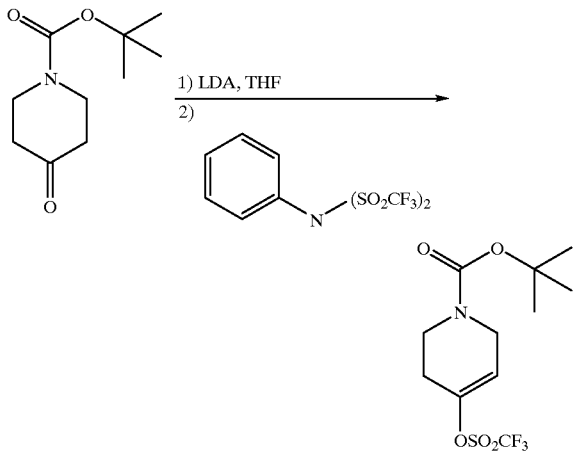

To a solution of diisopropylamine (13.4 ml, 0.096 mol) in tetrahydrofuran (400 ml), (cooled to −78° C. was added n-butyllithium (2.5 M in hexanes, 38.4 ml, 0.096 mol) followed by addition of 1-tert-butoxycarbonyl-4-piperidone (16 g, 0.080 mol) in tetrahydrofuran (200 ml). After stirring for 10 minutes, a solution of N-phenyltrifluoromethane sulfonimide (31.4 g, 0.088 mol) in tetrahydrofuran (100 ml) was added. The reaction mixture was stirred for 15 minutes at −78° C., allowed to warm to room temperature and quenched with saturated bicarbonate solution. The reaction was diluted with ether and washed with 15% potassium hydrogen sulfate, saturated bicarbonate solution, 1N sodium hydroxide×4, water×2 and brine. Drying and solvent evaporation gave a solid; flash chromatography (silica gel, hexane-ethyl acetate, 95:5) gave trifluoromethanesulfonic acid[1-tert-butoxycarbonyl-(1,2,3,6-tetrahydropyridin-4-yl)] ester.

$^1$H NMR (CDCl$_3$) δ 1.48 (s, 9H), 2.44 (m, 2H), 3.63 (t, 2H, J=5.6 Hz), 4.04 (d, 2H, J=2.6 Hz), 5,76 (bs, 1H).

Step B. 4-(2-Cyano-4-fluorophenyl)-3,6-dihydro-2H-pyridine-1-carboxylic Acid tert-butyl Ester A solution of 2-bromo-5-fluorobenzonitrile (8.1 g, 40.5 mmole) in THF (50 mL) was added rapidly to a solution of n-BuLi (20 mL, 2.5M, 50 mmole) in THF at −78° C. and the resulting solution is stirred for 5 minutes. To this solution was added ZnCl$_2$, (0.5 M in THF, 89 mL, mmoles) and the solution was warmed to 0° C. Palladium tetrakistiiphenylphosphine (1.5 g, 1.3 mmole) was added followed by trifluoromethanesulfonic acid [1-tert-butoxycarbonyl-(1,2,3,6-tetra-hydropyridin-4-yl)] ester from step A from above (9 g, 27.16 mmole). The reaction was heated to 40° C. for 30 minutes and then cooled to room temperature and poured into saturated aqueous sodium bicarbonate (1 L). The mixture was extracted with ethyl acetate (3×300 mL) and the combined organic extracts were dried over anhydrous magnesium sulfate, filtered and concentrated at reduced pressure. The residue was chromatographed on silic,a gel eluting with 15% to 30% ethyl acetate/hexanes to give the product.

$^1$H NMR (CDCl$_3$): δ 7.4–7.25 (m, 3H), 5.95 (br s, 1H), 4.09 (br s, 2H), 3.65–3.60 (m, 2H), 2.50 (m, 2H), 1.50 (s, 9H).

Step C. 4-(2-Cyano-4-fluorophenyl)-piperidine-1-carboxylic Acid tert-butyl Ester 4-(2-Cyano-4-fluorophenyl)-3,6-dihydro-2H-pyridine-1-carboxylic acid tert-butyl ester (7.89 g, 26.1 mmol) and 10% Palladium on carbon (3.95 g) were combined in absolute ethanol (270 ml) containing acetic acid (0.79 ml) and the mixture hydrogenated at 60 psi for 2.5 hrs. The catalyst was removed by filtration through super cel and the filtrate concentrated to dryness in vacuo to give a crude oil. Flash chromatography on silica gel (10% to 15% ethyl acetate in hexane) gave the product as a colorless oil.

$^1$H NMR (CDCl$_3$): δ 7.35–7.25 (m, 3H), 4.30–4.11 (br d, 2H), 3.15–3.06 (m, 1H), 2.91–2.82 (t, 2H), 1.87–1.82 (br d, 2H), 1.68–1.62 (m, 2H), 1.49 (s,9H).

Step D. 5-Fluoro-2-piperidin-4-yl-benzonitrile hydrochloride

An ethyl acetate solution (56 ml) of 4-(2-Cyano-4-fluorophenyl)-piperidine-1-carboxylic acid tert-butyl ester (5.64 g, 18.5 mmol) was cooled to 0° C. and hydrogen chloride gas was bubbled through the solution until saturated (10 min). The solution was stirred in the cold (20 min) and then concentrated in vacuo to give the product as a white solid.

$^1$H NMR (CD$_3$OD): δ 7.61–7.53 (m, 2H), 7.53–7.43 (m, 1H), 3.60–3.50 (m, 2H), 3.40–3.16 (m, 3H), 2.18–1.94 (m, 4H).

Step E. 2-[1-(3-Aminopropyl)-piperidin-4-yl]-4-fluoro benzonitrile hydrochloride A suspension of 2-(piperidin-4-yl)-4-fluorobenzonitrile hydrochloride (2.5 g, 10.4 mmol), 3-bromo-1-tertbutoxycarbonylpropylamine (3.22 g, 13.5 mmol) and triethylamine (3.76 ml, 27 mmol) in DMF (12 ml) was stirred at room temperature for 16 hours. The reaction mixture was diluted with ethyl acetate (200 mL) and washed with saturated bicarbonate solution, water×2 and brine. Drying and solvent evaporation gave after flash chromatography (silica gel, ethyl acetate) 3.1 g of 2-[1-(3-tert-butoxycarbonylaminopropyl) piperidin-4-yl]-4-fluorobenzonitrile. This material was dissolved in EtOAc (200 mL), cooled to 0° C. and HCl gas was bubbled into the solution for 15 minutes. The reaction mixture was concentrated at reduced pressure to give the title compound.

$^1$H NMR (CD$_3$OD): δ 7.65–7.50 (m, 2H), 7.5–7.43 (m, 1H), 3.75–3.65 (m, 2H), 3.40–3.1 (m, 3H), 2.25–2.1 (m, 4H).

EXAMPLE 2

3-[4-(4-Fluorophenyl)piperidin-1-yl]propylamine

Step A. 4-(4-Fluorophenyl)piperidine hydrochloride

To a solution of 4-(4-fluorophenyl)-1,2,3,6-tetrahydropyridine hydrochloride (10 g) in methanol (200 mL) was added 10% palladium on charcoal (0.5 g) and the mixture was hydrogenated at 50 psi for 3 h. The catalyst was removed by filtration and solvent was evaporated to leave the product as a white powder, which was used in the next step without any purification.

M.P. 181–182° C.

$^1$H NMR (CDCl$_3$): δ 1.95–2.03 (br d, 2H), 2.14–2.29 (m, 2H), 2.70–2.80 (m, 1H), 2.91–3.07 (br q, 2H), 3.60–3.64 (br d, 2H), 6.96–7.03 (m, 2H), (m, 2H), 9.60 (br s, 1H), 9.71 (br s, 1H).

Step B. 3-[4-(4-Fluorophenyl)piperidin-1-yl]propylphthalimide

A mixture of 4-(4-fluorophenyl)piperidine hydrochloride (5.08 g, 23.2 mmol), 3-bromopropylphthalimide (6.22 g, 23.2 mmol), and potassium carbonate (15 g) in DMF (100 mL) was stirred and heated at 95–100° C. for 12 h. About 80% of the solvent was evaporated at reduced pressure, the residue was diluted with ethyl acetate (200 mL) and washed with brine (3×100 mL) and dried (Na$_2$SO$_4$). Solvent was evaporated and the residue, was purified by column chromatography on silica gel using 1/1 hexane-ethyl acetate to 100% ethyl acetate as eluent. This product was crystallized from isopropanol to give a white crystalline solid; m.p. 80–81° C. This material was used in the next step. Concentration of the mother liquor and cooling gave the second crop.

$^1$H NMR (CDCl$_3$): δ 1.43–1.52 (m, 2H), 1.67–1.75 (m, 2H), 1.80–1.96 (m, 4H), 2.33–2.46 (m, 3H), 2.94–2.99 (br d, 2H), 3.78 (t, J=7 Hz, 2H), 6.90–7.04 (m, 4H), 7.70–7.74 (m, 2H), 7.84–7.87 (m, 2H).

Step C. 3-[4-(4-Fluorophenyl)piperidin-1-yl]propylamine

To a solution of 3-[4-(4-fluorophenyl)piperidin-1-yl] propylphthalimide (4.5 g, 12.3 mmol) in methanol (200 mL) was added 4 ml or hydrazine and the mixture was refluxed for 8 h. It was cooled, and the white solid was filtered and washed with methanol (20 mL). Solvent was evaporated, and the residue was dried under vacuum for 4 h. Chloroform (50 mL) was added to this material, it was stirred for 1 h and filtered. The white solid was washed with more chloroform (20 mL), and the solvent was evaporated from the combined filtrates to leave the crude product as an oil. It was purified by column chromatography on silica gel using dichloromethane/methanol/2M ammonia in methanol (10/3/1) as the eluent.

$^1$H NMR (CDCl$_3$): δ 1.60–1.83 (m, 6H), 1.96–2.07 (m, 4H), 2.40–2.55 (m, 3H), 2.70–2.85 (br t, 2H), 3.03–3.07 (br d, 2H), 6.93–7.00 (m, 2H), 7.14–7.20 (m, 2H).

EXAMPLE 3

2-[1-(3-Aminopropyl)-piperidin-4-yl]benzonitrile hydrochloride

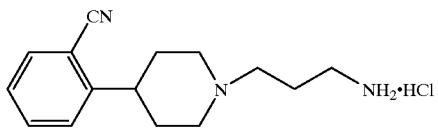

Step A. Trifluoromethanesulfonic acid[1-tert-butoxycarbonyl-(1,2,3,6-tetrahydro-pyridin-4-yl)]Ester The title compound was prepared as described in Step A of Example 1.

Step B. 2-[1-tertbutoxycarbonyl-(1,2,3,6-tetrahydropyridin-4-yl)]benzonitrile

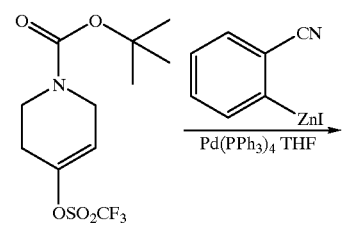

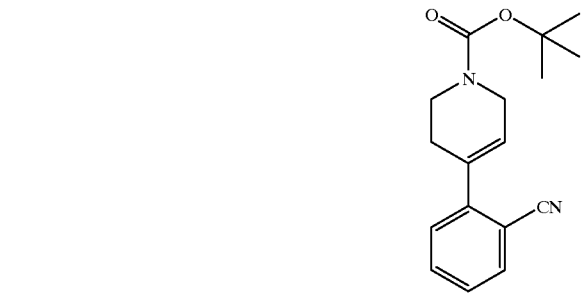

To a suspension of trifluoromethanesulfonic acid[1-tert-butoxycarbonyl-(1,2,3,6-tetrahydropyridin-4-yl)] ester (10.5 g, 0.032 mol) and tetrakis(triphenylphosphine) palladium(0) (1.8 g, 1.6 mmol) in tetrahydrofuran (95 ml) was added iodo(2-cyaniophenyl)zinc (0.5M in tetrahydrofuran, 94 ml, 0.047 mol) dropwise. The reaction mixture was stirred at room temperature for 0.5 hours and quenched with saturated bicarbonate solution. The mixture was diluted with ethyl acetate and washed with weater×2 and brine. Drying and solvent evaporation gave an oil; flash chromatography (silica gel, hexane-ethyl acetate, 92:8) gave the title compound.

$^1$H NMR (CDCl$_3$): δ 1.50 (s, 9H), 2.53 (m, 2H), 3.67 (t, 2H, J=6.0 Hz), 4.12 (d, 2H, J=3.2 Hz), 5.98 (m, 1H), 7.34 (m, 2H), 7.54 (bt, 1H, J=7.6 Hz), 7.66 (bd, 1H, J=8 Hz).

Step C. 2-(1-tert-Butoxycarbonylpiperidin-4-yl)benzonitrile

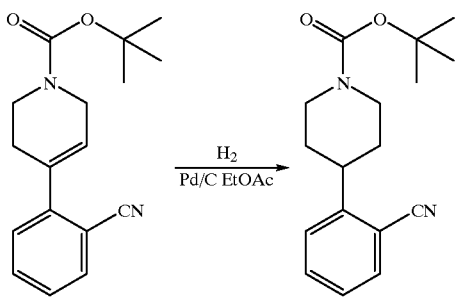

To a solution of 2-[1-tert-butoxycarbonyl-(1,2,3,6-tetrahydropyridin-4-yl)]benzonitrile (5.3 g, 0.019 mol) and acetic acid (0.28 ml, 4.9 mmol) in ethanol (200 ml), degassed with argon was added palladium on carbon. The reaction was hydrogenated on a Parr apparatus at 50 psi for 15 hours. The mixture was recharged twice with acetic acid (0.14 ml, 0.28 ml) and palladium on carbon (900 mg, 1.8 g), hydrogenated as above and filtered through celite. Solvent evaporation gave 2-(1-tert-butoxycarbonylpiperidin-4-yl) benzonitrile.

$^1$H NMR (CDCl$_3$): δ 1.49 (s, 9H), 1.64 (m, 2H), 1.86 (bd, 2H, J=13.4 Hz), 2.88 (bt, 2H, J=14 Hz), 3.14 (tt, 1H, J=12 Hz, J=4 Hz), 4.27 (bs, 2H), 7.31 (m, 2H), 7.56 (bt, 1H, J=7.7 Hz), 7.63 (bd, 1H, J=7.7 Hz).

Step D. 2-(Piperidin-4-yl)benzonitrile hydrochloride

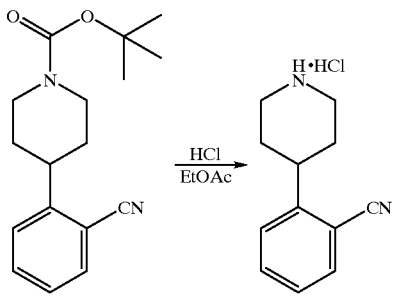

To a solution of 2-(1-tertbutoxycarbonylpiperidin-4-yl) benzonitrile (1.7 g, 5.9 mmol) in ethyl acetate (~50 ml), cooled to 0° C. was added hydrogen chloride gas, bubbled vigorously for 5 minutes. The reaction mixture was stirred for 10 minutes at 0+ C., purged with argon and concentrated. Flushing with ethyl acetate×3 and concentration gave 2-(piperidin-4-yl)benzonitrile hydrochloride;

$^1$H NMR (DMSO): δ 1.98 (m, 4H), 3.07 (m, 2H), 3.21 (tt, 1H, J=12 Hz, J=3.8 Hz), 3.36 (m, 2H), 7.46 (m, 2H), 7.74 (bt, 1H, J=7.7 Hz), 7.83 (bd, 1H, J=7.0 Hz), 9.10 (bd, 2H).

Step E. 3-Bromo-1-tertbutoxycarbonylpropylamine

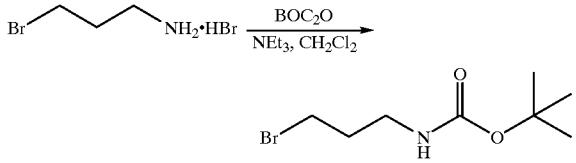

To a suspension of 3-bromopropylamine hydrobromide (5.0 g, 0.023 mol) and di-tert-butyl dicarbonate (5.0 g, 0.023 mol) in methylene chloride (125 ml), cooled to 0° C. was added triethylamine (3.2 ml, 0.023 mol). The reaction mixture was stirred for 3 hours at room temperature, diluted with methylene chloride and washed with water×2 and brine. Drying and solvent evaporation gave 3-bromo-1-tert-butoxycarbonylpropylamine.

$^1$H NMR (CDCl$_3$): δ 1.46 (s, 9H), 2.05 (m, 2H), 3.28 (m, 2H), 3.43 (m, 2H), 4.64 (bs, 1H).

Step F. 2-[1-(3-tert-Butoxycarbonylaminopropyl) piperidin-4-yl] benzonitrile

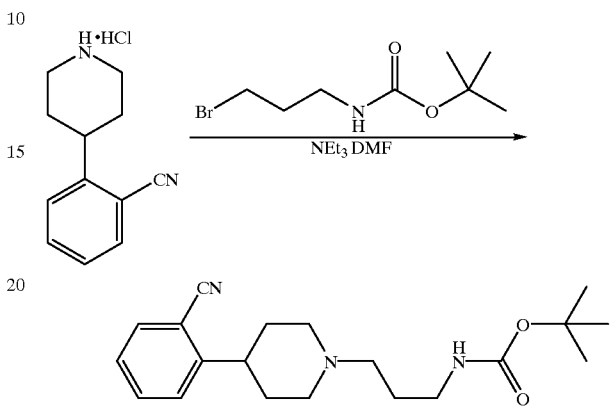

A suspension of 2-(piperidin-4-yl)benzonitrile hydrochloride (600 mg, 2.7 mmol), 3-bromo-1-tert-butoxycarbonylpropylamine (0.67 g, 2.8 mmol) and triethylamine (0.77 ml, 5.5 mmol) in DMF (12 ml) was stirred at room temperature for 15 hours. The reaction mixture was diluted with ethyl acetate and washed with saturated bicarbonate solution, water×2 and brine. Drying and solvent evaporation gave an oil (0.86 g); flash chromatography (silica gel, ethyl acetate) gave 2-[1-(3-tert-butoxycarbonylaminopropyl) piperidin-4-yl] benzonitrile.

$^1$H NMR (CDCl$_3$): δ 1.45 (s, 9H), 1.69 (m, 2H), 1.80 (bt, 2H, J=12 Hz), 1.89 (m, 2H), 2.12 (bt, 2H, J=10.8 Hz), 2.47 (t, 2H, J=6.7 Hz), 2.97–3.08 (m, 3H), 3.22 (m, 2H), 5.61 (bs, 1H), 7.29 (m, 1H), 7.39 (bd, 1H, J=7.9 Hz), 7.54 (bt, 1H, J=7.7 Hz), 7.62 (bd, 1H, J=7.7 Hz).

Step G. 2-[1-(3-Aminopropyl)-piperidin-4-yl]benzonitrile hydrochloride

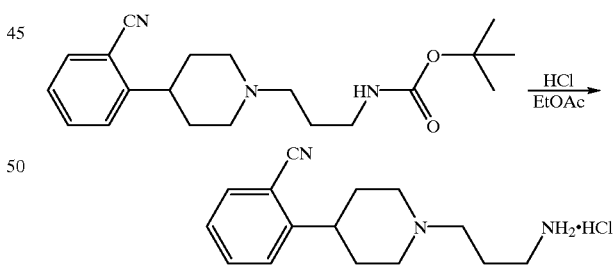

To a solution of 2-[1-(3-tert-butoxycarbonylaminopropyl)piperidin-4-yl] benzonitrile (0.73 g, 2.1 mmol) in ethyl acetate (100 ml), cooled to 0° C. was added hydrogen chloride gas, bubbled vigorously for 5 minutes. The reaction mixture was stirred for 10 minutes at 0° C., purged with argon and concentrated. Flushing with ethyl acetate×2 and concentration gave 2-[1-(3-aminopropyl)-piperidin-4-yl] benzonitrile hydrochloride.

$^1$H NMR (DMSO): δ 2.00 (m, 2H), 2.10 (m, 2H), 2.28 (m, 2H), 2.95 (m, 2H), 3.18 (m, 4H), 3.56 (bd, 2H, J=11.7 Hz), 7.47 (m, 2H), 7.75 (bt, 1H, J=8 Hz), 7.84 (bd, 1H, J=7.9 Hz), 8.14 (bs, 2H), 11.1 (bd, 1H).

EXAMPLE 4

1-(3-Aminopropyl)-4-(2,4-difluorophenyl)-piperidine-4-carbonitrile dihydrochloride

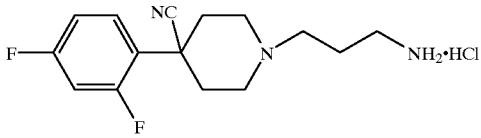

Step A. Bis-(2-chloro-ethyl)-tert-butoxycarbonylamine

To a solution of bis(2-chloroethyl)amine hydrochloride (10 g, 56.7 mmol) in 2.5:1 dioxane:H₂O (210 mL) was added triethylamine (7.9 mL, 56.7 mmol). This solution was cooled to 0° C. under argon, and di-tert-butyldicarbonate (15.0 g, 68.6 mmol) was added. This was stirred for 45 min, poured onto saturated sodium bicarbonate, and extracted with ethyl acetate. The combined organic layers were washed with saturated sodium chloride, dried with magnesium sulfate, and concentrated in vacuo to give the product.

$^1$H NMR (CDCl$_3$): δ 3.70–3.55 (m, 8H), 1.47 (s, 9H).

Step B. 4-(2,4-Difluorophenyl)-tert-butoxycarbonylpiperidine-4-carbonitrile

To a solution of bis-(2-chloro-ethyl)-tert-butoxycarbonylamine (20.1 g, 83.8 mmol) in DMF (200 mL) was added 2,4-difluorobenzylacetonitrile (10 g, 76.2 mmol). This solution was cooled to 0° C., and a 60% dispersion of sodium hydride was added portion wise (6.6 g, 166 mmol). The solution was stirred for 20 min, warmed to room temperature, then stirred at room temperature 1.5 h. The reaction was then poured onto water, and extracted with ethyl acetate (3×250 mL). The combined organic layers were washed with saturated sodium chloride, dried with magnesium sulfate, and concentrated in vacuo. The crude material was passed through silica (25% ethyl acetate, hexane) to give the product.

$^1$H NMR (CDCl$_3$): δ 7.50–7.35 (m, 1H), 7.0–6.85 (m, 2H), 4.40–4.10 (br m, 2H), 3.40–3.10 (br m, 2H), 2.25–2.10 (m, 2H), 2.15–1.95 (m, 2H), 1.49 (s, 9H).

Step C. 4-(2,4-Difluorophenyl)-piperidine-4-carbonitrile hydrochloride

A solution of 4-(2,4-difluorophenyl)-tert-butoxycarbonylpiperidine-4-carbonitrile (12.5 g, 40.7 mmol) in 250 mL ethyl acetate was cooled to 0° C. Hydrogen chloride gas wais bubbled through the solution for 10 min. The solid that seperated was collected by filtration and dried overnight under vacuum to give the product.

$^1$H NMR (CD$_3$OD): δ 7.65–7.55 (m, 1H), 7.20–7.05 (m, 2H), 3.70–3.60 (m, 2H), 3.45–3.00 (m, 2H), 2.60–2.50 (m, 2H), 2.50–2.35 (m, 2H).

Step D. 1-(3-tert-Butoxycarbonylamino-propyl)-4-(2,4-difluorophenyl)-piperidine-4-carbonitrile To a solution of 4-(2,4-difluorophenyl)-piperidine-4-carbonitrile (4 g, 15.5 mmol) in DMF (50 mL) was added 3-bromopropyl-tert-butoxycarbonylamine (4 g, 17 mmol) and triethylainine (4.7 mL, 34 mmol) under argon. The solution was stirred 2 days at ambient temperature, poured into saturated sodium bicarbonate (500 mL), and extracted with ethyl acetate (2×250 mL). The combined organic layers were washed with saturated sodium chloride, dried with magnesium sulfate, and concentrated in vacuo. The crude material was chroinatographed on silica (2% methanol in dichloromethmne) to give the product (4.3 g).

$^1$H NMR (CDCl$_3$): δ 7.50–7.45 (m, 1H), 6.95.–6.80 (m, 2H), 5.37 (br s, 1H), 3.25–3.15 (m, 2H), 3.1–3.0 (m, 2H), 2.6–2.4 (m, 4H), 2.3–2.1 (m, 4H), 1.75–1.60 (m, 2H).

Step E. 1-(3-Aminopropyl)-4-(2,4-difluorophenyl)-piperidine-4-carbonitrile dihydrochloride A solution of 1-(3-tert-butoxycarbonylamino-propyl)-4-(2,4-difluorophenyl)piperidine-4-carbonitrile (4.3 g) in 80 mL ethyl acetate was cooled to 0° C. Hydrogen chloride gas was bubbled through the solution for 10 min. The solid that seperated was collected by filtration and dried in vauo to give the product (2.5 g).

$^1$H NMR (CD$_3$OD): δ 7.66–7.55 (m, 1H), 7.21–7.05 (m, 2H), 3.94–3.82 (m, 2H), 3.50–3.30 (m, 4H), 3.15–3.05 (m, 2H), 2.70–2.55 (m, 4H), 2.30–2.15 (m, 2H).

EXAMPLE 5

1-(3-Amino-propyl)-4-cyanophenyl)-piperidine-4-carbonitrile hydrochloride

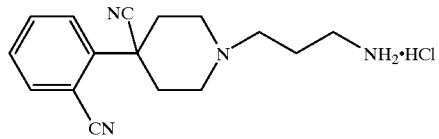

Step A: Bis(2-chloroethyl)-N-(1,1-dimethylethoxy)carbonyl amine

A solution of N-(2,2'-bischloro)diethyl amine (23.0 g, 0.130 mol) and di-tert-butyl dicarbonate (28.8 g, 0.130 mol) in CH$_2$Cl$_2$ (150 mL) was treated with N,N-diisopropylethylamine (22.52 ml, 0.720 mol) at room temperature (1.5 h). The solvent was removed in vacuo and the residue was triturated with ether (300 ml). The ether solution was collected and concentrated in vacuo affording N-(2,2'-bischloro)-diethyl-N-(1,1-dimethylethoxy)carbonyl amine as a clear oil.

$^1$H NMR (CDCl$_3$): δ 3.65 (m, 8H), 1.52 (s, 9H).

FAB MS (3:1 mixture of dithiothreitol and dithioerythritol in MeOH) m/e 242 g/mole (M$^+$+H, C$_{25}$H$_{29}$N$_2$O$_5$SCl=242.2 g/mole.)

Step B: 4-Cyano-N-(1,1-dimethylethoxy)carbonyl-4-(2-cyanophenyl) piperidine

A solution of bis(2-chloroethyl)-N-(1,1-dimethylethoxy)carbonyl amine (19 g, 78 mmol) and homophthalonitrile (8.6 g, 60 mmol) and cesium carbonate (79 g, 241 mmol) was stirred at 60° C. for 12 hours. The solution cooled to room temperature and diluted with 500 ml EtOAc and washed with saturated aqueous NaHSO$_4$ and saturated aqueous NaCl. The solution was dried over Na$_2$SO$_4$, concentrated in vacuo, and purified by PCTLC (30% EtOAc in Hexane) to afforded 4-cyano-N-(1,1-dimethylethloxy)carbonyl-4-(2-cyanophenyl) piperidine as a yellow/orange oil.

$^1$H NMR (CDCl$_3$): δ 7.81–7.79 (d, 2H), 7.67–7.65 (m, 2H), 7.51–7.47 (m, 1H), 4.31 (br s, 2H), 3.26 (br s, 2H), 2.33–2.20 (m, 4H), 1.48 (s, 9H).

Step C: 4-Cyano-4-(2-cyanophenyl)piperidine hydrochloride

A solution of EtOAc saturated with HCl (200 ml) was added to 4-cyano-N-(1,1-dimethylethoxy)carbonyl-4-(2-methylphenyl)piperidine (1.5 g, 5.7 mmol). The resulting mixture was allowed to react for 1 hour at room temperature. The EtOAc was removed in vacuo affording 1.5 g of 4-cyano-4-(2-cyanophenyl)piperidine hydrochloride as a yellow solid.

Step D: 4-(2-Cyanophenyl)-4-cyano-N-(3-[N-{1,1-dimethyl ethoxycarbonyl}]amino)propylpiperidine A solution of 4-(2-cyanophenyl)-4-cyanopiperidine hydrochloride (0.5 g, 2.01 mmol) and N,N-diisopropylethylamine (0.421 ml, 2.42 mmole) in DMF (5 mL) at 0° C. was added sodium hydride (0.0968 g, 2.42 mmol). The slurry stirred for 1 hour at 0° C. and was then added N-(3-bromopropyl)-N-(1,1-dimethylethoxy)carbonyl amine (0.480 g, 2.01 mmol) in DMF (3 mL). The solution stirred for 12 hours at room temperature. The reaction was quenched by the addition of water. The product was extracted with EtOAc (2×50 ml) and washed with $H_2O$ (2×25 ml). The solvent was dried over $Na_2SO_4$, concentrated in vacuo, and purified by PCTLC (5% MeOH in $CHCl_3$). 4-(2-Cyanophenyl)-4-cyano-N-[3-{N-(1,1-dimethyl-ethoxy)carbonyl}amino]propyl piperidine was obtained as an oil.

$^1$H NMR ($CDCl_3$): δ 7.80–7.78 (dd, 1H), 7.67–7.59 (m, 2H), 7.49–7.45 (m, 1H), 5.14 (br s, 1H), 3.21–3.20 (d, 2H), 3.09–3.06 (d, 2H), 2.58–2.51 (m, 2.43–2.40 (d, 2H), 2.30–2.25 (m, 2H), 1.73–1.66 (m, 2H), 1.56 (s, 1H), 1.43 (s, 9H).

Step E: N-(3-amino)propyl-4-(2-cyanophenyl)-4-cyanopiperidine dihydrochloride

The title compound was prepared using the same procedure described above in Step C for the preparation of 4-cyano-4-(2-cyanophenyl)piperidine hydrochloride.

EXAMPLE 6

(4S,5R)-4-(3,4-Difluorophenyl)-5-hydroxymethyl-2-oxo-oxazolidine-3-carboxylic acid {3-[4-(2-cyano-4-fluorophenyl)piperidin-1-yl]propyl}amide

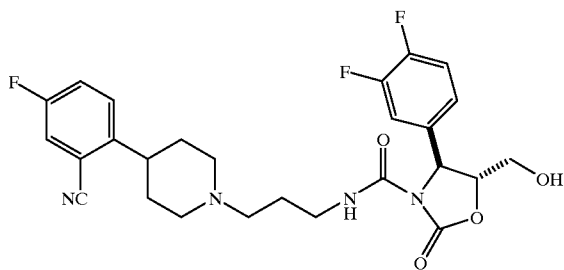

Step A: trans-3,4-Difluorocinnamic acid methyl ester

To a solution of trans-3,4-difluorocinnamic acid (10 g, 54 mmol) in 300 mL methanol was added concentrated sulfuric acid (2 mL). The solution was stirred 48 h at ambient temperature and then concentrated in vacuo. The residue was taken up in ethyl acetate (500 mL) and washed with saturated sodium bicarbonate (2×100 mL), brine (1×100 mL), dried with magnesium sulfate, and concentrated in vacuo to provide trans-3,4-difluorocinnamic acid methyl ester as a white solid.

$^1$H NMR ($CDCl_3$): δ 7.59 (d, 1H, J=15.9), 7.34 (m, 1H), 7.24 (m, 1H) 7.18 (dd, 1H, J=9.9, 2.0), 6.35 (d, 1H, J=16.1), 3.81 (s, 3H).

Step B: (2R, 3S)-N-Benzyloxycarbonyl-3-amino-3-(3,4-difluorophenyl)-2-hydroxypropionic acid methyl ester A solution of NaOH (4.1 g, 103 mmol) was prepared in 175 mL water. Potassium osmate dihydrate (491 mg, 1.3 mmol) was dissolved in 35 mL of this NaOH solution, resulting in a dark pink homogeneous mixture. To a 1000 mL round bottom flask is added the remaining NaOH solution prepared above, 135 mL n-propanol and benzyl carbamate (9.8 g, 110 mmol). The suspension was stirred at ambient temperature for 30 min wherein the mixture was nearly homogeneous. The reaction flask was placed in a room temperature water bath and the surrounding lights were turned off. Freshly prepared t-butylhypochlorite (11.2 mL, 103 mmol) was added dropwise with vigorous stirring, and the reaction stirred an additional 15 min. In a separate 250 mL round bottom flask was suspended trans-3,4-difluorocinnamic acid methyl ester (6.6 g, 33.3 mmol) and $(DHQ)_2PHAL$ (1.3 g, 1.7 mmol) in 100 mL n-propanol. The suspension was added to the above reaction mixture and the residue rinsed into the reaction flask (2×10 mL). To the reaction was added the above prepared solution of potassium osmate dihydrate. The resulting green solution became amber/brown over 1 h. Sodium metabisulfite (66 g, 347 mmol) was added and the resulting suspension stirred 3 h when it was poured into a separatory funnel containing ethyl acetate (200 mL) and the layers separated. The aqueous layer was extracted with ethyl acetate (150 mL) and the combined organics washed with brine (100 mL), dried with magnesium sulfate, and concentrated in vacuo to provide a pale yellow solid. The crude material was passed through silica (25% ethyl acetate/hexane) to give (2R,3S)-N-benzyloxycarbonyl-3-amino-3-(3,4-difluorophenyl)-2-hydroxypropionic acid methyl ester contaminated with benzyl carbamate.

Step C: (2R, 3S)-3-Amino-3-(3,4-difluorophenyl)-2-hydroxypropionic acid methyl ester (2R, 3S)-N-Benzyloxycarbonyl-3-amino-3-(3,4-difluorophenyl)-2-hydroxypropionic acid methyl ester (>12.2 g, 33.3 mmol maximum) was dissolved in 750 mL ethanol. The flask was purged with argon and palladium on carbon (2 g, 10% wt) was added. The suspension was then purged, filled with hydrogen, and stirred 16 h. The suspension was piirged with argon, filtered through celite and concentrated in vacuo to give (2R,3S)-3-amino-3-(3,4-difluorophenyl)-2-hydroxypropionic acid methyl ester from trans-3,4-difluorocinnamic acid methyl ester).

$^1$H NMR ($CDCl_3$): δ 7.26 (m, 1H), 7.15–7.08 (m, 2H), 4.28 (s, 2H), 3.82 (s, 3H), 2.48 (bs, 2H).

Step D: (4S,5R)-4-(3,4-Difluorophenyl)-2-oxo-oxazolidine-5-carboxylic Acid methyl Ester To a solution of (2R,3S)-3-amino-3-(3,4-difluorophenyl)-2-hydroxypropionic acid methyl ester (5.8 g, 25 mmol) in 250 mL tetrahydrofuran at 0° C. was added N,N-diisopropylethylamine (8.75 mL, 50 mmol) and triphosgene (2.48 g, 8.4 mmol). The reaction was stirred at 0° C. for 30 min when it was poured over ethyl acetate (200 mL) and saturated sodium carbonate solution (100 mL). The layers were separated, the organic layer washed with saturated sodium carbonate solution (1×100 mL), dried with magnesium sulfate, and concentrated in vacuo to provide a pale yellow oil. The material svas triturated with 25% ethyl acetate/hexane to provide (4S,5R)-4-(3,4-difluorophen)fl)-2-oxo-oxazolidine-5-carboxylic acid methyl ester. The recovered mother liquor was passed through silica (50% ethyl acetate/hexane) to give additional product.

$^1$H NMR ($CDCl_3$): δ 7.25–7.20 (m, 2H), 7.15 (m, 1H), 6.33 (bs, 1H), 4.98 (d, 1H, J=5.1), 4.72 (d, 1H, J=5.3), 3.89 (s, 3H).

FABMS M+H=258.

Step E: (4S,5R)4-(3,4-Difluorophenyl)-5-hydroxymethyl-oxazolidin-2-one

To a solution of (4S,5R)-4-(3,4-difluorophenyl)-2-oxo-oxazolidine-5-carboxylic acid methyl ester (200 mg, 0.8 mmol) in tetrahydrofuran (10 mL) at 0° C. was added a 2 M solution of lithium borohydride in tetrahydrofuran (0.4 mL, 0.8 mmol). After stirring for 20 min at 0° C., saturated sodium bicarbonate (20 mL) was added and the mixture stirred at ambient temperature for 20 min. Ethyl acetate (50 mL) was added and the layers separated. The organic layer was washed with brine (1×10 mL), dried with magnesium sulfate, filtered and concentrated in vacuo to provide (4S, 5R) 4-(3,4-difluorophenyl)-5-hydroxymethyl-oxazolidin-2-one as a white solid.

¹H NMR (CDCl₃): δ 7.23–7.15 (m, 2H), 7.10–7.07 (m, 1H), 6.48 (bs, 1H), 4.89 (d, 1H, J=6.8), 4.31 (dt, 1H, J=6.6, 2.9), 3.96 (dd, 1H, J=12.82, 2.75), 3.70 (bdd, 1H, J=12.1, 2.2), 3.53 (bs, 1H).

Step F: (4S,5R) 4-(3,4-Difluorophenyl)-5-(tetrahydropyran-2-yloxymethyl)-oxazolidin-2-one To a solution of (4S,5R) 4-(3,4-difluorophenyl)-5-hydroxymethyl-oxazolidin-2-one (695 mg, 3.0 mmol) in dry dichloromethane (30 mL) was added 2,3-dihydropyran (0.3 mL, 3.6 mmol) and 10-camphorsulfonic acid (70 mg, 0.3 mmol). The reaction mixture was stirred at ambient temperature for 3 h. The reaction mixture was diluted with dichloromethane (100 mL), washed with saturated sodium bicarbonate solution (2×100 ml), brine (1×100 ml), dried over magnesium sulfate and filtered. The volatiles were removed under reduced pressure and the resulting solid was purified by pressurized silica gel chromatography (1:1 then 2:1 ethyl acetate:hexane) to afford (4S,5R)-4-(3,4-difluorophenyl)-5-(tetrahydropyran-2-yloxymethyl)-oxazolidin-2-one as a colorless oil.

FAB MS: m/z=314 (M+H).

Step G: (4S,5R)-4-(3,4-Difluorophenyl)-2-oxo-5-(tetrahydropyran-2-yloxymethyl)-oxazolidine-3-carboxylic acid 4-nitrophenyl ester To a solution of (4S,5R)-4-(3,4-difluorophenyl)-5-(tetrahydropyran-2-yloxymethyl)-oxazolidin-2-one (910 mg, 2.9 mmol) in anhydrous tetrahydrofuran (60 mL) cooled to −78° C. under argon, was added a 1 M solution of lithium bis(trimethylsilyl)amide in tetrahydrofuran (2.9 mL, 2.9 mmol) dropwise. The reaction mixture was warmed to 0° C. in an ice bath, stirred 45 min, and then returned to −78° C. In a separate flask, p-nitrophenylchloroformate (586 mg, 2.9 mmol) was dissolved in anhydrous tetrahydrofuran (50 mL) under argon and cooled to −78° C. The above prepared anion solution was added via cannula to the chloroformate solution and reaction mixture was stirred 1 h at −78° C. The reaction mixture was treated with ethyl acetate (150 mL). The resulting solution was washed with water (1×150 ml), brine (1×150 mL), dried over magnesium sulfate and filtered. The volatiles were removed under reduced pressure to give (4S,5R)-4-(3,4-difluorophenyl)-2-oxo-5-(tetrahydropyran-2-yloxymethyl)-oxazolidine-3-carboxylic acid 4-nitrophenyl ester as a yellow foam.

FAB MS: m/z=479 (M+H).

Step H: (4S,5R)-4-(3,4-Diiluorophenyl)-5-(tetrahydropyran-2-yloxymethyl)-2-oxo-oxazolidine-3-carboxylic acid {3-[4-(2-cyano-4-fluorophenyl)piperidin-1-yl]propyl}amide To a suspension of 2-[1-(3-aminopropyl)piperidin-4-yl]-5-fluorobenzonitrile dihydrochloride (100 mg, 0.30 mmol) (see Example 1) in dry tetrahydrofuran (6 mL) was added N,N-diisopropylethylamine (107 μL, 0.6 mmol) followed by (4S,5R)-4-(2,4-difluorophenyl)-2-oxo-5-(tetrahydropyran-2-yloxymethyl)-oxazolidine-3-carboxylic acid 4-nitrophenyl ester (143 mg, 0.30 mmol). The reaction mixture was stirred at room temperature for 2 h when the reaction was diluted with ethyl acetate (50 mL), washed with 10% aqueous sodium carbonate solution (8×50 mL), dried over magnesium sulfate and filtered. The volatiles were removed under reduced pressure and the resulting oil was purified by pressurized silica gel chromatography (0–1% methanol in ethyl acetate) to afford (4S,5R)-4-(3,4-difluorophenyl)-5-(tetrahydropyran-2-yloxymethyl)-2-oxo-oxazolidine-3-carboxylic acid {3-[4-(2-cyano-4-fluorophenyl)piperidin-1-yl]propyl}amide as an oil.

Step I: (4S,5R)-4-(3,4-Difluorophenyl)-5-hydroxymethyl-2-oxo-oxazolidine-3-carboxylic acid {3-[4-(2-cyano-4-fluorophenyl)piperidin-1-yl]propyl}amide To a solution of (4S,5R)-4-(3,4-difluorophenyl)-5-(tetrahydropyran-2-yloxymethyl)-2-oxo-oxazolidine-3-carboxylic acid {3-[4-(2-cyano-4-fluorophenyl)piperidin-1-yl]propyl}amide (122 mg, 0.20 mmol) in methanol (5 mL) was added p-toluenesulfonic acid (38 mg, 0.20 mmol). The reaction mixture was stirred at room temperature for 18 h. The volatiles were removed under reduced pressure, the residue taken up in ethyl acetate (100 mL), washed with 10% sodium carbonate solution (2×50 mL), dried over magnesium sulfate and filtered. The volatiles were removed under reduced pressure to afford (4S,5R)-4-(3,4-difluorophenyl)-5-hydroxymethyl-2-oxo-oxazolidine-3-carboxylic acid {3-[4-(2-cyano-4-fluorophenyl)piperidin-1-yl]propyl}amide. The hydrochloride salt was prepared according to standard procedures to provide a white solid.

FAB MS: m/z=517 (M+H).

Analysis: Calcd for C26 H27 N4 O4 F3.0.55 H₂O.HCl

C, 55.47, H, 5.21, N, 9.95.
Found: C, 55.46, H, 5.51, N, 9.84.

EXAMPLE 7

(4S,5R)-4-(3,4-Difluorophenyl)-5-hydroxymethyl-2-oxo-oxazolidine-3-carboxylic acid {3-[4-(4-fluorophenyl)piperidin-1-yl]propyl}amide

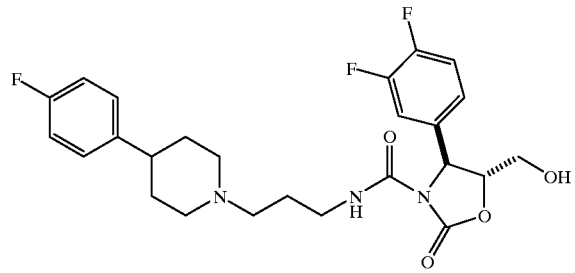

The title compound was prepared by a procedure substantially as described above in Example 1, Steps H and I, wherein 3-[4-(4-fluorophenyl) piperidin-1-yl]propylamine (see Example 2) was employed in place of 2-[1-(3-aminopropyl)piperidin-4-yl]-5-fluorobenzonitrile dihydrochloride.

FAB MS: m/z=492 (M+H).

Analysis: Calcd for C25 H28 N3 O4 F3.H2O

C, 58.93, H, 5.93, N, 8.25.
Found: C, 58.90, H, 6.11, N, 8.13.

EXAMPLE 8

(4S,5R)-4-(3,4-Difluorophenyl)-5-hydroxymethyl-2-oxo-oxazolidine-3-carboxylic acid {3-[4-(2-cyanophenyl)piperidin-1-yl]propyl}amide

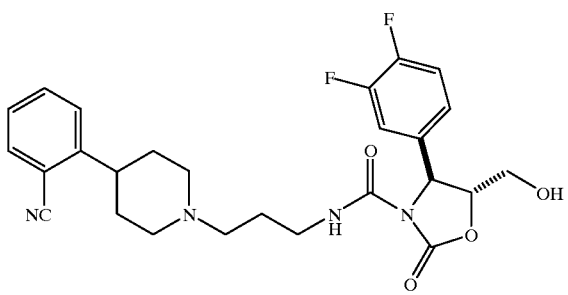

The title compound was prepared by a procedure substantially as described above in Example 1, Steps H and I, wherein 2-[1-(3-aminopropyl)-piperidin-4-yl] benzonitrile hydrochloride (see Example 3) was employed in place of 2-[1-(3-aminopropyl)piperidin-4-yl]-5-fluorobenzonitrile dihydrochloride.

FAB MS: m/z=499 (M+H).

Analysis:

Calcd for C26 H28 N4 O4
F2.HCl.0.85H2O.0.55EtOAc
C, 56.56, H, 5.91, N, 9.36.
Found: C, 56.57, H, 5.37, N, 9.38.

EXAMPLE 9

(4S,5R)-4-(3,4-Difluorophenyl)-5-hydroxymethyl-2-oxo-oxazolidine-3-carboxylic acid {3-[4-cyano-4-(2,4-difluorophenyl)piperidin-1-yl]propyl}amide

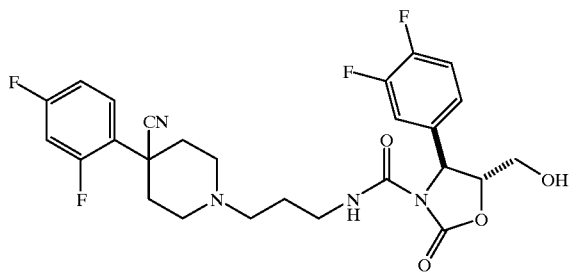

The title compound was prepared by a procedure substantially as described above in Example 1, Steps H and I, wherein 1-(3-aminopropyl)-4-(2,4-difluorophenyl)-piperidine-4-carbonitrile dihydrochloride (see Example 4) was employed in place of 2-[1-(3-aminopropyl)piperidin-4-yl]-5-fluorobenzonitrile dihydrochloride.

FAB MS: m/z=535 (M+H).

Analysis: Calcd for C26 H26 N4 O4 F4.1.3H2O.HCl

C, 52.53, H, 5.02, N, 9.43.
Found: C, 52.53, H, 4.94, N, 9.13.

EXAMPLE 10

(4S,5R)-4-(3,4-Difluorophenyl)-5-hydroxymethyl-2-oxo-oxazolidine-3-carboxylic acid {3-[4-cyano-4-(2-cyanophenyl)piperidin-1-yl]propyl}amide

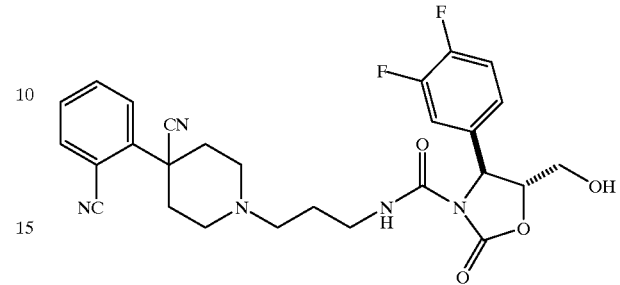

The title compound was prepared by a procedure substantially as described above in Example 1, Steps H and I, wherein 1-(3-amino-propyl)-4-cyanophenyl)-piperidine-4-carbonitrile hydrochloride (see Example 5) was employed in place of 2-[1-(3-aminopropyl)piperidin-4-yl]-5-fluorobenzonitrile dihydrochloride.

FAB MS: m/z=524 (M+H).

EXAMPLE 11

(4S,5R)-4-(3,4-Difluorophenyl)-5-methoxymethyl-2-oxo-oxazolidine-3-carboxylic acid {3-[4-(2-cyanophenyl)piperidin-1-yl]propyl}amide

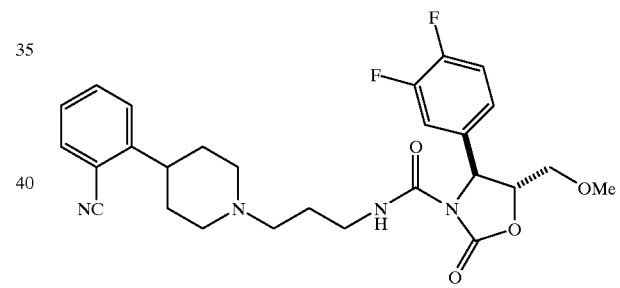

Step A: (4S,5R)4-(3,4-Difluorophenyl)-5-methoxymethyl-oxazolidin-2-one

To a solution of (4S,5R)-4-(3,4-difluorophenyl)-5-hydroxymethyl-oxazolidin-2-one (130 mg, 0.57 mmol, prepared as in Example 1, Step E) in dry acetonitrile (22 mL) was added silver(I)oxide (0.66 g, 2.8 mmol) and methyl iodide (353 mL, 5.7 mmol). The reaction flask was covered to prevent exposure to light and the reaction mixture stirred at ambient temperature for 20 h when it was filtered through celite and the volatiles removed in vacuo. The resulting oil was purified by pressurized silica gel chromatography (50–80% ethyl acetate in hexane) to afford (4S,5R)-4-(3,4-difluorophenyl)-5-methoxymethyl-oxazolidin-2-one as a colorless oil.

FAB MS: m/z=244 (M+H).

Step B: (4S,5R)-4-(3,4-Difluorophenyl)-2-oxo-5-methoxymethyl-oxazolidine-3-carboxylic acid 4-nitrophenyl Ester To a solution of (4S,5R)-4-(3,4-difluorophenyl)-5-methoxymethyl-oxazolidin-2-one (156 mg, 0.64 mmol) in anhydrous tetrahydrofuran (5 mL) cooled to −78 C under argon, was added a 1 M solution of lithium bis (trimethylsilyl)amide in tetrahydrofuran (0.64 mL, 0.64 mmol) dropwise. The reaction mixture was warmed to 0° C. in an ice bath, stirred 45 min, and then returned to −78° C. Meanwhile, in a separate dried flask, the p-nitrophenylchloroformate (129 mg, 0.64 mmol) was dissolved in anhydrous tetrahydrofuran (3 mL) under argon and cooled to −78° C. The above prepared anion solution was added via cannula to the chloroformate solution and reaction mixture was stirred 1.5 h at −78° C. The reaction mixture was treated with ethyl acetate (50 mL). The resulting solution was washed with brine (2×50 mL), dried over magnesium sulfate and filtered. The volatiles were removed under reduced pressure to give (4S,5R)-4-(3,4-difluorophenyl)-2-oxo-5-methoxymethyl-oxazolidine-3-carboxylic acid 4-nitrophenyl ester as a foam.

Step C: (4S,5R)-4-(3,4-Difluorophenyl)-5-methoxymethyl-2-oxo-oxazolidine-3-carboxylic acid {3-[4-(2-cyanophenyl)piperidin-1-yl]propyl}amide To a solution of (4S,5R)-4-(3,4-difluorophenyl)-2-oxo-5-methoxymethyl-oxazolidine-3-carboxylic acid 4-nitrophenyl ester (195 mg, 0.48 mmol) in dry tetrahydroftirin (3 mL) was added 2-[1-(3-aminopropyl)piperidin-4-yl]benzonitrile dihydrochloride (134 mg, 0.48 mmol) (see Example 3) followed by N,N-diisopropylethylamine (167 μL, 0.96 mmol). The reaction mixture was stirred at room temperature for 20 h when the reaction was diluted with ethyl acetate (50 mL), washed with 10% aqueous sodium carbonate solution (6×25 mL), dried over magnesium sulfate and filtered. The volatiles were removed under reduced pressure and the resulting oil was purified by pressurized silica gel chromatography (2% methanol in ethyl acetate) to afford an oil. The hydrochloride salt was prepared by standard procedures to provide (4S,5R)-4-(3,4-difluorophenyl)-5-methoxymethyl-2-oxo-oxazolidine-3-carboxylic acid {3-[4-(2-cyanophenyl)piperidin-1-yl] propyl}amide hydrochloride as a white solid.

FAB MS: m/z=513 (M+H).
Analysis: Calcd for C27 H30 N4 O4 F2.HCl.1.2H$_2$O
C, 56.73, H, 6.07, N, 9.80.
Found: C, 56.71, H, 5.72, N, 9.43.

EXAMPLE 12

(4S,5R)-4-(3,4-Difluorophenyl)-5-methoxymethyl-2-oxo-oxazolidine-3-carboxylic acid {3-[4-cyano-4-(2,4-difluorophenyl)piperidin-1-yl]propyl}amide

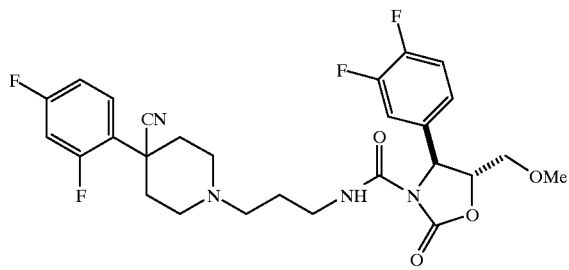

The title ccompound was prepared by a procedure substantially as described above in Example 11, Step C, wherein 1-(3-aminopropyl)-4-(2,4-difluorophenyl)-piperidine-4-carbonitrile dihydrochloride (see Example 4) was employed in place of 2-[1-(3-aminopropyl)piperidin-4-yl]benzonitrile dihydrochloride.

FAB MS: m/z=549 (M+H).
Analysis: Calcd for C27 H28 N4 O4 F4.HCl.H$_2$O
C, 53.77, H, 5.18, N, 9.29.
Found: C, 53.77, H, 5.14, N, 9.28.

EXAMPLE 13

(4S,5R)-4-(3,4-Difluorophenyl)-5-methoxymethyl-2-oxo-oxazolidine-3-carboxylic acid {3-[4-(2-cyano-4-fluorophenyl)piperidin-1-yl]propyl}amide

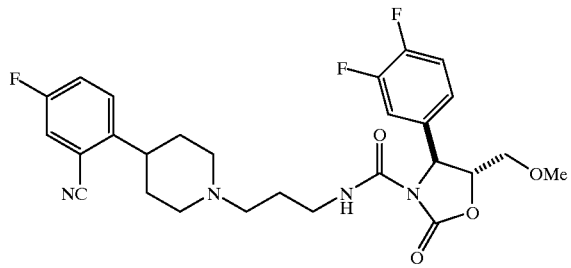

The title compound was prepared by a procedure substantially as described above in Example 11, Step C, wherein 2-[1-(3-aminopropyl)-piperidin-4-yl]-5-fluorobenzonitrile hydrochloride (see Example 1) was employed in place of 2-[1-(3-aminopropyl)piperidin-4-yl]benzonitrile dihydrochloride.

FAB MS: m/z=531 (M+H).

EXAMPLE 14

As a specific embodiment of an oral composition, 100 mg of the compound of Example 6 is formulated with sufficient finely divided lactose to provide a total amount of 580 to 590 mg to fill a size O hard gel capsule.

EXAMPLE 15

Screening Assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 μl) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligzLnd. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 16

Selective Binding Assays

Membranes prepared from stably transfected human alpha 1d and alpha 1b cell lines (ATCC CRL 1138 and CRL 11139, respectively) were used to identify compounds that selectively bind to the human alpha 1a adrenergic receptor. These competition binding) reactions (total volume=200 μl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

All of the compounds of the present invention prepared in Examples 6–13 were found to have alpha 1a Ki values of less than 1 nM, as determined via the screening assay described in Example 15. All of the compounds were further found to be more than 100-fold more selective in binding to alpha 1a receptors versus binding to the alpha 1b and alpha 1d receptors, as determined via the selective binding assay described in the preceding paragraph. All of the compounds except for those of Examples 11 (1a about 184-fold more selective than 1b) and 13 (1a about 453-fold more selective than 1b) were greater than 500-fold more selective in binding to alpha 1a receptors versus alpha 1b and 1d receptors.

EXAMPLE 17

Exemplary Counterscreens

1. Assay Title: Dopamine D2, D3, D4 in vitro screen
   Objective of the Assay:
   The objective of this assay is to eliminate agents which specifically affect binding of [3H] spiperone to cells expressing human dopamine receptors D2, D3 or D4.
   Method:
   Modified from VanTol et al., *Nature* (1991), 350: 610–613.
   Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 µg membranes in a total volume of 500 µl containing 0.2 nM [3H]-spiperone. Non-specific binding is defined using 10 µM apomorphine. The assay is terminated after a 2 hour incubation at room temperature by rapid filtration over GF/B filters presoaked in 0.3% PEI, using 50 mM Tris-HCl pH 7.4.

2. Assay Title: Serotonin 5HT1a
   Objective of the Assay
   The objective of this assay is to eliminate agents which specifically affect binding to cloned human 5HT1a receptor
   Method:
   Modified from Schelegel and Peroutka, *Biochemical Pharmacology* (1986), 35: 1943–1949.
   Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl2 and 1 mg/ml ascorbate. Non-specific binding is defined using 10 µM propranolol. The assay is terminated after a 1 hour incubation at room temperature by rapid filtration over GF/Cfilters.

EXAMPLE 18

Exemplary Functional Assays

In order to confirm the specificity of compounds for the human alpha 1a adrenergic receptor and to define the biological activity of the compounds, the following functional tests may be performed:

1. In vitro Rat, Dog and Human Prostate and Dog Urethra
   Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.

The tissue is placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% $CO_2$/95% $O_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.

After a single priming dose of 3 µM (for rat), 10 µM (for dog) and 20 µM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.

$EC_{50}$ value:; are calculated for each group using Graph-Pad Inplot software. $pA_2$ (-log $K_b$) values were obtained from Schild plot when three or more concentrations were tested. When less than three concentrations of antagonist are tested, $K_b$ values are calculated according to the following formula $K_b$=[B],
   where x is the ratio of $EC_{50}$ of agonist in the presence and absence of antagonist and [B] is the antagonist concentration.

2. Measurement of Intra-Urethral Pressure in Anesthetized Dogs
   PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephline, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four parameter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Shild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A compound of formula:

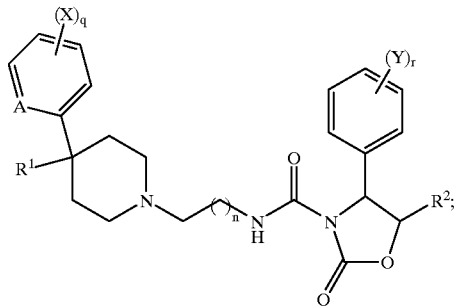

wherein A is CX or N;

X is hydrogen, halo, nitro, cyano, hydroxy, $C_1$–$C_4$ alkyl, $C_1$–$C_4$ alkoxy, fluorinated $C_1$–$C_4$ alkyl, fluorinated $C_1$–$C_4$ alkoxy, $(CH_2)_{1-4}OR^a$, $C_3$–$C_8$ cycloalkyl, fluorinated $C_3$–$C_8$ cycloalkyl, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^a)_2$, or $(CH_2)_{0-4}SO_2R^a$;

Y is hydrogen, halo, nitro, cyano, hydroxy, $C_1$–$C_4$ alkyl, $C_1$–$C_4$ alkoxy, fluorinated $C_1$–$C_4$ alkyl, fluorinated $C_1$–$C_4$ alkoxy, $(CH_2)_{1-4}OR^a$, $C_3$–$C_8$ cycloalkyl, fluorinated $C_3$–$C_8$ cycloalkyl, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^a)_2$, or $(CH_2)_{0-4}SO_2R^a$;

$R^1$ is hydrogen, cyano, $CO_2R^a$, $C(=O)N(R^a)_2$, $C_1$–$C_6$ alkoxy, tetrazole, phenyl, or mono- or poly-substituted phenyl; wherein each of the substituents on the substituted phenyl is independently selected from halo, nitro, cyano, hydroxy, $N(R^a)_2$, $N(R^a)C(=O)R^a$, $N(R^a)C(=O)N(R^a)_2$, $NR^aSO_2R^a$, $NR^aSO_2N(R^a)_2$, $C_1$–$C_6$ alkyl, $C_3$–$C_8$ cycloalkyl, $C_1$–$C_6$ alkoxy, fluorinated $C_1$–$C_6$ alkyl, fluorinated $C_3$–$C_8$ cycloalkyl, fluorinated $C_1$–$C_6$ alkoxy, $(CH_2)_{1-4}OR^a$, $(CH_2)_{0-4}CO_2R^a$, $(CH_2)_{0-4}C(=O)N(R^a)_2$, $(CH_2)_{0-4}SO_2N(R^a)_2$, and $(CH_2)_{0-4}SO_2R^a$;

$R^2$ is $CH_2OR^b$;

$R^a$ is hydrogen, $C_1$–$C_6$ alkyl, or fluorinated $C_1$–$C_6$ alkyl;

$R^b$ is hydrogen, or $C_1$–$C_6$ alkyl;

n is an integer of from 1 to 3; and q and r are each independently integers of from 0 to 3;

or a pharmaceutically acceptable salt thereof.

2. The compound according to claim 1, wherein the compound is of formula

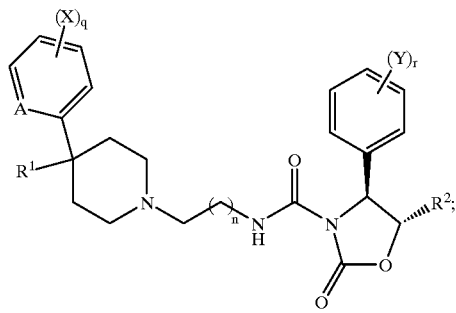

or a pharaceutically acceptable salt thereof.

3. The compound according to claim 1, wherein

X is hydrogen, halo, nitro, cyano, hydroxy, $C_1$–$C_4$ alkyl, $C_1$–$C_4$ alkoxy, $(CH_2)_{1-3}OR^a$, $(CH_2)_{0-3}CF_3$, $OCF_3$, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^a)_2$, or $(CH_2)_{0-4}SO_2R^a$;

Y is hydrogen, halo, nitro, cyano, hydroxy, $C_1$–$C_4$ alkyl, $C_1$–$C_4$ alkoxy, $(CH_2)_{1-3}OR^a$, $(CH_2)_{0-3}CF_3$, $OCF_3$, $N(R^a)_2$, $N(R^a)COR^a$, $N(R^a)CON(R^a)_2$, $N(R^a)SO_2R^a$, $N(R^a)SO_2N(R^a)_2$, $(CH_2)_{0-4}CO_2R^a$, $(CH_2)_{0-4}CON(R^a)_2$, $(CH_2)_{0-4}SO_2N(R^a)_2$, or $(CH_2)_{0-4}SO_2R^a$;

$R^1$ is hydrogen, cyano, $CO_2R^a$, $C(=O)N(R^a)_2$, $C_1$–$C_4$ alkoxy, or tetrazole;

$R^a$ is hydrogen, $C_1$–$C_4$ alkyl, or $(CH_2)_{0-3}CF_3$; and q and r are each independently integers of from 0 to 2;

or a pharmaceutically acceptable salt thereof.

4. The compound according to claim 3, wherein

A is CX; and $R^b$ is hydrogen, or $C_1$–$C_4$ alkyl;

or a pharmaceutically acceptable salt thereof.

5. The compound according to claim 4, wherein

X is hydrogen, halo, nitro, cyano, hydroxy, methyl, ethyl, methoxy, ethoxy, or $CF_3$;

Y is hydrogen, halo, nitro, cyano, hydroxy, methyl, ethyl, methoxy, ethoxy or $CF_3$;

$R^1$ is hydrogen, cyano, $CO_2CH_3$, $CO_2CH_2CH_3$, methoxy, or ethoxy; and $R^2$ is $CH_2OH$ or $CH_2OCH_3$;

or a pharmaceutically acceptable salt thereof.

6. The compound according to claim 5, wherein

X is hydrogen, fluoro or cyano; and

Y is hydrogen or fluoro;

or a pharmaceutically acceptable salt thereof.

7. The compound according to claim 5, wherein the compound is of formula

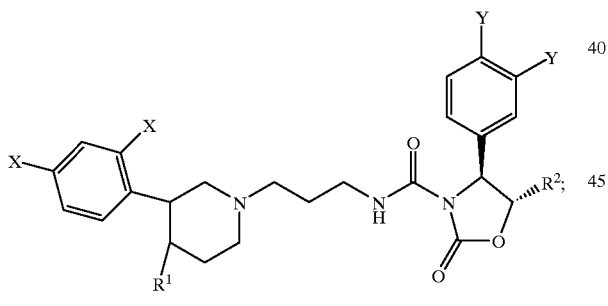

or a pharmaceutically acceptable salt thereof.

8. The compound according to claim 7, wherein

X is hydrogen, fluoro or cyano; and

Y is hydrogen or fluoro;

or a pharmaceutically acceptable salt thereof.

9. The compound according to claim 8, wherein the compound is selected from the group consisting of:

(4S,5R)-4-(3,4-difluorophenyl)-5-hydroxymethyl-2-oxo-oxazolidine-3-carboxylic acid {3-[4-(2-cyano-4-fluorophenyl)piperidin-1-yl]propyl}amide;

(4S,5R)-4-(3,4-difluorophenyl)-5-hydroxymethyl-2-oxo-oxazolidine-3-carboxylic acid {3-[4-(4-fluorophenyl)piperidin-1-yl]propyl}amide;

(4S,5R)-4-(3,4-difluorophenyl)-5-hydroxymethyl-2-oxo-oxazolidine-3-carboxylic acid {3-[4-(2-cyanophenyl)piperidin-1-yl]propyl}amide;

(4S,5R)-4-(3,4-difluorophenyl)-5-hydroxymethyl-2-oxo-oxazolidine-3-carboxylic acid {3-[4-cyano-4-(2,4-difluorophenyl)piperidin-1-yl]propyl}amide;

(4S,5R)-4-(3,4-difluorophenyl)-5-hydroxymethyl-2-oxo-oxazolidine-3-carboxylic acid {3-[4-cyano-4-(2-cyanophenyl)piperidin-1-yl]propyl}amide;

(4S,5R)-4-(3,4-difluorophenyl)-5-methoxymethyl-2-oxo-oxazolidine-3-carboxylic acid {3-[4-(2-cyanophenyl)piperidin-1-yl]propyl}amide;

(4S,5R)-4-(3,4-difluorophenyl)-5-methoxymethyl-2-oxo-oxazolidine-3-carboxylic acid {3-[4-cyano-4-(2,4-difluorophenyl)piperidin-1-yl]propyl}amide;

(4S,5R)-4-(3,4-difluorophenyl)-5-methoxymethyl-2-oxo-oxazolidine-3-carboxylic acid {3-[4-(2-cyano-4-fluorophenyl)piperidin-1-yl]propyl}amide; and pharmaceutically acceptable salts thereof.

10. The compound according to claim 9, wherein the compound is (4S,5R)-4-(3,4-difluorophenyl)-5-hydroxymethyl-2-oxo-oxazolidine-3-carboxylic acid {3-[4-(2-cyano-4-fluorophenyl)piperidin-1-yl]propyl}amide, having the structure

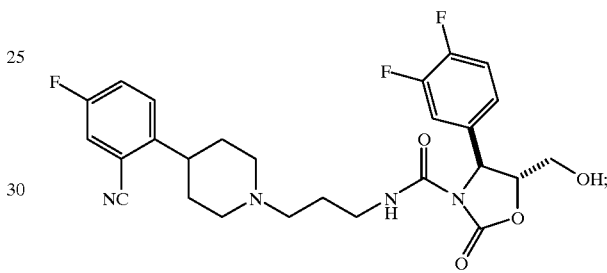

or a pharmaceutically acceptable salt thereof.

11. The compound according to claim 9, wherein the compound is (4S,5R)-4-(3,4-difluorophenyl)-5-hydroxymethyl-2-oxo-oxazolidine-3-carboxylic acid {3-[4-cyano-4-(2,4-difluorophenyl)piperidin-1-yl]propyl}amide, having the structure

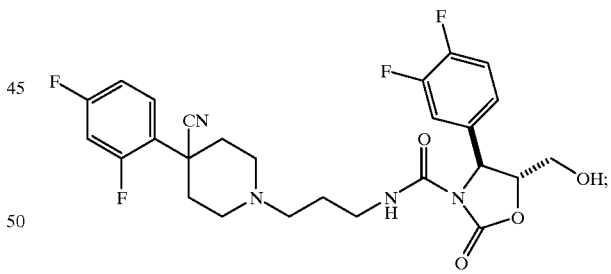

or a pharmaceutically acceptable salt thereof.

12. A pharmaceutical composition comprising the compound according to claim 1 and a pharmaceutically acceptable carrier.

13. A pharmaceutical composition made by combining the compound according to claim 1 and a pharmaceutically acceptable carrier.

14. A process for making a pharmaceutical composition comprising combining the compound according to claim 1 and a pharmaceutically acceptable carrier.

15. The composition according to claim 12 further comprising a testosterone 5-alpha reductase inhibitor.

16. The composition according to claim 15, wherein the testosterone 5-alpha reductase inhibitor is a type 1, a type 2, both a type 1 and a type 2 or a dual type 1 and type 2, testosterone 5-alpha reductase inhibitor.

17. The composition according to claim 16, wherein the testosterone 5-alpha reductase inhibitor is a type 2 testosterone 5-alpha reductase inhibitor.

18. The composition according to claim 17, wherein the testosterone 5-alpha reduclase inhibitor is finasteride.

19. A method of treating benign prostatic hyperplasia in a subject in need thereof which comprises administering to the subject a therapeutically effective amount of the compound according to claim 1.

20. The method according to claim 19, wherein the compound does not cause a fall in blood pressure at dosages effective to alleviate benign prostatic hyperlasia.

21. The method according to claim 19, wherein the compound is administered in combination with a testosterone 5-alpha reductase inhibitor.

22. The method according to claim 21, wherein the testosterone 5-alpha reductase inhibitor is finasteride.

23. A method of treating benign prostatic hyperplasia in a subject in need thereof which comprises administering a therapeutically effective amount of the composition according to claim 12.

24. The method according to claim 23, wherein the composition further comprises a therapeutically effective amount of a testosterone 5-alpha reductase inhibitor.

25. A method of relaxing lower urinary tract tissue in a subject in need thereof which comprises administering to the subject a therapeutically effective amount of the compound according to claim 1.

26. The method according to claim 25, wherein the compound is administered in combination with a testosterone 5-alpha reductase inhibitor.

27. The method according to claim 26, wherein the testosterone 5-alpha reductase inhibitor is finasteride.

28. A method of treating a condition which is susceptible to treatment by antagonism of the alpha 1a receptor which comprises administering to a subject in need thereof an amount of the compound according to claim 1 effective to treat the condition.

29. A method of eliciting an alpha 1a antagonizing effect in a mammal in need thereof, comprising administering to the mammal a therapeutically effective amount of the compound according to claim 1.

* * * * *